US 6,650,916 B2

(12) United States Patent
Cook et al.

(10) Patent No.: US 6,650,916 B2
(45) Date of Patent: **\*Nov. 18, 2003**

(54) METHOD AND APPARATUS FOR PROVIDING HIGH CONTRAST IMAGING

(75) Inventors: Christopher A. Cook, Philadelphia, PA (US); Mark M. Meyers, Exton, PA (US)

(73) Assignee: Cytoprop, L.L.C., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/067,783

(22) Filed: Feb. 8, 2002

(65) Prior Publication Data

US 2002/0111546 A1 Aug. 15, 2002

Related U.S. Application Data

(63) Continuation of application No. 09/401,859, filed on Sep. 22, 1999, now Pat. No. 6,438,396.
(60) Provisional application No. 60/107,203, filed on Nov. 5, 1998.

(51) Int. Cl.[7] .................................................. A61B 5/00
(52) U.S. Cl. ..................................................... 600/322
(58) Field of Search ............................... 600/310, 322, 600/365, 473, 330, 162, 476, 309, 250; 356/39–42, 364, 369; 382/128, 130, 134, 274

(56) References Cited

U.S. PATENT DOCUMENTS

| | | | |
|---|---|---|---|
| 3,999,855 A | 12/1976 | Hirschfeld | 356/338 |
| 5,058,596 A | 10/1991 | Makino et al. | 600/476 |
| 5,526,116 A | 6/1996 | de Groot | 356/512 |
| 5,598,842 A | 2/1997 | Ishihara et al. | 128/637 |
| 5,636,633 A | 6/1997 | Messerschmidt et al. | 600/368 |
| 5,791,345 A | 8/1998 | Ishihara et al. | 600/368 |
| 5,873,821 A | 2/1999 | Chance et al. | 600/310 |
| 5,983,120 A | 11/1999 | Groner et al. | 600/310 |
| 5,995,856 A | 11/1999 | Mannheimer et al. | 600/322 |
| 6,112,114 A | 8/2000 | Dreher | 600/476 |
| 6,438,396 B1 * | 8/2002 | Cook et al. | 600/310 |

OTHER PUBLICATIONS

Born, M. and Wolf, E., *Principle of Optics: Electromagnetic Theory of Propagation Interference and Diffraction of Light*, Sixth Edition, Cambridge University Press, pp. 522–526 (1980).
Hecht–Zajac, *Optics*, Addison–Wesley Publishing Company, pp. 219–274 (1974).
Smith, W., *Modern Optical Engineering*, 2nd Edition, McGraw–Hill, p. 229 (1990).

* cited by examiner

*Primary Examiner*—Eric F. Winakur
*Assistant Examiner*—Matthew J Kremer
(74) *Attorney, Agent, or Firm*—Caesar, Rivise, Bernstein, Cohen & Pokotilow, Ltd.

(57) ABSTRACT

An in vivo imaging device having an illumination system that creates a virtual source within a tissue region of a subject in a non-invasive manner. The illumination system transforms a maximum amount of illumination energy from a light source into a high contrast illumination pattern. The illumination pattern is projected onto the object plane in a manner that maximizes the depth to which clear images of sub-surface features can be obtained. The high intensity portion of the illumination pattern is directed onto the object plane outside the field of view of an image capturing device that detects the image. In this configuration, scattered light from within the tissue region interacts with the object being imaged. This illumination technique provides for a high contrast image of sub-surface phenomena such as vein structure, blood flow within veins, gland structure, etc.

30 Claims, 14 Drawing Sheets

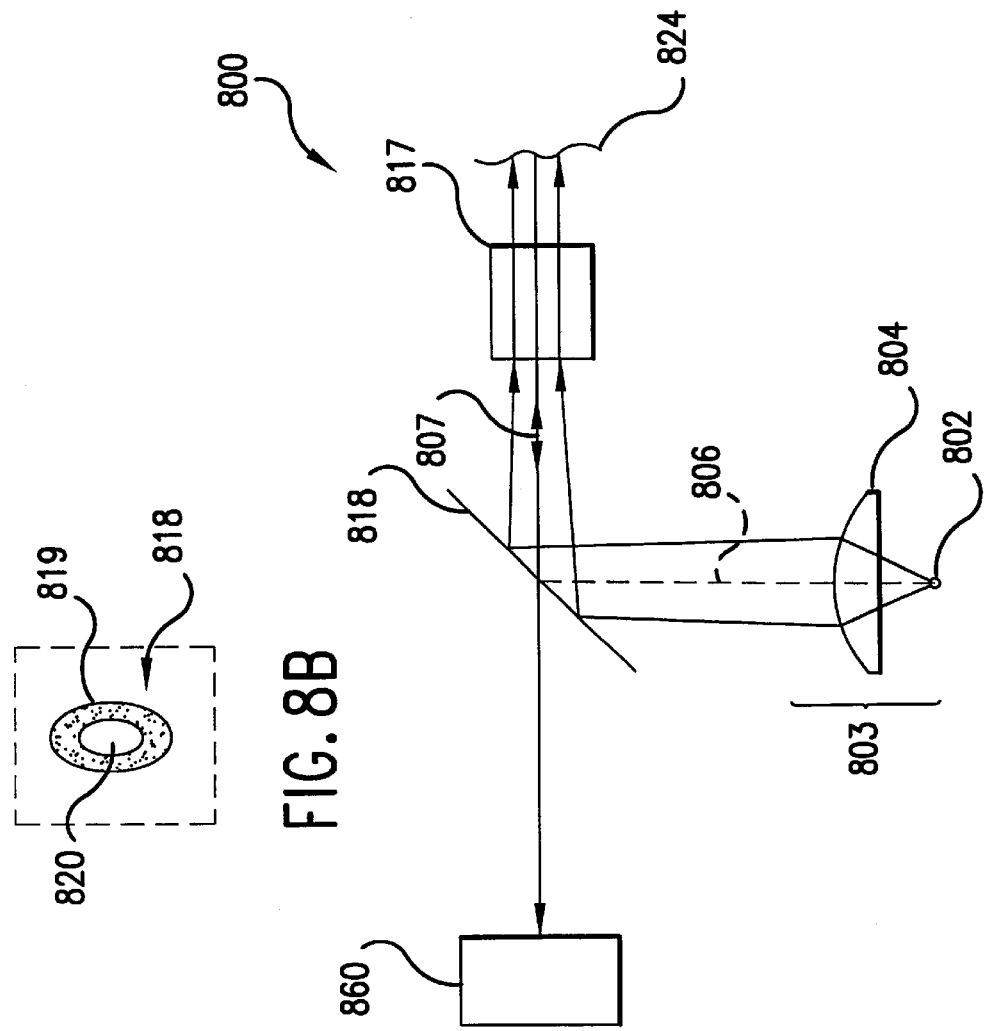

METHOD AND APPARATUS FOR PROVIDING HIGH CONTRAST IMAGING

RELATED APPLICATION

This application is a Continuation application of Ser. No. 09/401,859 (now U.S. Pat. No. 6,438,396), filed on Sep. 22, 1999 and whose entire disclosure is incorporated by reference herein. The present application claims priority of Ser. No. 09/401,859 under 35 U.S.C. §120 which in turn claims priority of No. 60/107,203 filed on Nov. 5, 1998.

BACKGROUND OF THE INVENTION

1. Field of the Invention

The present invention is related to imaging analysis. More particularly, the present invention is related to the use of imaging to perform non-invasive spectral imaging analysis of a subject's vascular system.

2. Related Art

Most widely accepted methods of blood testing and analysis require invasive and in vitro techniques. For example, a conventional complete blood count including the white blood cell differential (CBC+Diff) test is done in an "invasive" manner in which a sample of venous blood is drawn from a patient through a needle, and submitted to a laboratory for analysis. Alternatively, it is often necessary to measure other types of blood components, such as non-cellular constituents (e.g., blood gases and bilirubin) present in the plasma component of blood. The most common method for bilirubin analysis is through an in vitro process. In such an in vitro process, a blood sample is invasively drawn from the patient. The formed elements (red blood cells and other cells) are separated by centrifugation and the remaining fluid is reacted chemically and analyzed spectrophotometrically.

Invasive techniques, such as for conventional CBC+Diff tests and bilirubin analysis, pose particular problems for newborns, elderly patients, burn patients, and patients in special care units. Thus it is desirable to utilize a device which is able to rapidly and non-invasively quantitatively measure a variety of blood and vascular characteristics. Such a technique would eliminate the need to draw a venous blood sample to ascertain blood characteristics. A device of this type would also eliminate the delay in waiting for the laboratory results in the evaluation of the patient. Such a device also has the advantage of added patient comfort.

Soft tissue, such as mucosal membranes or unpigmented skin, do not absorb light in the visible and near-infrared, i.e., they do not absorb light in the spectral region where hemoglobin absorbs light. This allows the vascularization to be differentiated by spectral absorption from surrounding soft tissue background. However, the surface of soft tissue strongly reflects light and the soft tissue itself effectively scatters light after penetration of only 100 microns. Therefore, in vivo visualization of the circulation is difficult because of poor resolution, and generally impractical because of the complexities involved in compensating for multiple scattering and for specular reflection from the surface. The resolution of such images is limited because of the scattering of light, and the computations to compensate for scattering are complex.

Spectrophotometry involves analysis based on the absorption or attenuation of electromagnetic radiation by matter at one or more wavelengths. The instruments used in this analysis are referred to as spectrophotometers. A simple spectrophotometer includes: a source of radiation, such as, e.g., a light bulb; a means of spectral selection such as a monochromator containing a prism or grating, or a colored filter; and one or more detectors, such as, e.g., photocells, which measure the amount of light transmitted and/or reflected by the sample in the selected spectral region.

In opaque samples, such as solids or highly absorbing solutions, the radiation reflected from the surface of the sample may be measured and compared with the radiation reflected from a non-absorbing or white sample. If this reflectance intensity is plotted as a function of wavelength, it gives a reflectance spectrum. Reflectance spectra are commonly used in matching colors of dyed fabrics or painted surfaces. However, because of its limited dynamic range and inaccuracy, reflection or reflectance spectrophotometry has been used primarily in qualitative rather than quantitative analysis. On the other hand, transmission spectrophotometry is conventionally used for quantitative analysis because Beer's law (inversely relating the logarithm of measured intensity linearly to concentration) can be applied.

Reflectance spectrophotometry is not a primary choice for quantitative analysis because specularly reflected light from a surface limits the available contrast (black to white or signal to noise ratio), and, consequently, the measurement range and linearity. Because of surface effects, measurements are usually made at an angle to the surface. However, only for the case of a Lambertian surface will the reflected intensity be independent of the angle of viewing. Light reflected from a Lambertian surface appears equally bright in all directions (cosine law). However, good Lambertian surfaces are difficult to obtain. Conventional reflectance spectrophotometry presents an even more complicated relationship between reflected light intensity and concentration than exists for transmission spectrophotometry which follows Beer's law. Under the Kubelka-Munk theory applicable in reflectance spectrophotometry, the intensity of reflected light can be related indirectly to concentration through the ratio of absorption to scattering.

Several devices for in vivo analysis based on reflectance spectrophotometry have been developed recently. However, these conventional reflectance-based devices are less than optimal for several reasons.

For example, one such device uses image analysis and reflectance spectrophotometry to measure individual cell parameters such as cell size. Measurements are taken only within small vessels, such as capillaries where individual cells can be visualized. Because this device takes measurements only in capillaries, measurements made by the device will not accurately reflect measurements for larger vessels. Other devices utilize light application means that focus an illumination source directly onto a blood vessel in a detection region. As a result, these devices are extremely sensitive to movements of the device with respect to the patient. This increased sensitivity to device or patient movement can lead to inconsistent results. To counteract this motion sensitivity, these devices require stabilizing and fixing means.

Other conventional devices have been developed based on traditional dark field illumination techniques. As understood in traditional microscopy, dark field illumination is a method of illumination which illuminates a specimen but does not admit light directly to the objective. For example, one traditional dark field imaging approach is to illuminate an image plane such that the angular distribution of illuminating light and the angular distribution of light collected by an objective for imaging are mutually exclusive. However, these devices are subject to scattering off optically active tissue in the image path which creates an orientation dependent backscatter or image glare that reduces image contrast. Moreover, rotation of these devices causes a change in contrast.

Thus, there is a need for a device that provides for complete non-invasive, in vivo analysis of the vascular system with high image quality. There is a need for a device that provides high resolution visualization of: blood cell components (red blood cells, white blood cells, and platelets); blood rheology; the vessels in which blood travels; and vascularization throughout the vascular system. There is a further need for a device that can minimize the glare and other deleterious artifacts arising in conventional reflectance spectrophotometric systems.

SUMMARY OF THE INVENTION

The present invention is directed to a method and apparatus for analysis of a sub-surface object, such as blood or tissue under the skin of a patient, by use of a high contrast illumination technique. In one embodiment, the device includes a light source, an illumination system, and an imaging system. The light source provides an illumination beam that propagates along an illumination path between the light source and the plane in which the object is located (the object plane). The illumination system transforms the illumination beam into a high contrast illumination pattern and projects that illumination pattern onto the sub-surface object. The illumination pattern has a high intensity portion and a low intensity portion. The imaging system includes an image capturing device that detects an image of the sub-surface object.

According to the present invention, the image of the object is formed by scattered illumination from the high contrast illumination pattern that is transmitted through the sub-surface object and propagates along an image path to the image capturing device. Further, the high intensity portion of the illumination pattern is incident on the object plane outside a field of view of the image capturing device.

In a preferred embodiment, the device further includes an illumination pattern generator that transforms the illumination beam into a high contrast illumination pattern. In this embodiment, a relay lens projects the illumination pattern onto the object plane. In a further embodiment of the present invention, an obscuration is used to block a portion of the illumination beam. Alternatively, a conical lens (also referred to as an axicon), a conical grating, or a holographic optical element is used to generate a high contrast illumination pattern.

In a further aspect of the present invention, the apparatus includes crossed polarizers that act to prevent any polarized light reflected off the surface of the sub-surface object or reflected off birefringent tissue layers in the near field from reaching the image capturing device.

A further aspect of the present invention provides a method for creating a source of illumination within a sub-surface tissue region that contains an object of interest in a non-invasive manner. The object is illuminated about an object plane wherein the object is located and is detected by an image capturing device. In a first step, a source of light is provided. Next, the light from the source is transformed into a high contrast illumination pattern having a high intensity portion and a low intensity portion. The illumination pattern is directed onto a surface of the tissue region such that the high intensity portion of the illumination pattern is incident upon the object plane outside a field of view of the image capturing device. According to the present invention, the high intensity portion of the illumination pattern undergoes one or more scattering events within the tissue region. Next, the scattered light that interacts with the object is detected by the image capturing device. According to the present invention, a substantial portion of the scattered light is transmitted through the object thus providing an image of the object that is detected by the image capturing device.

BRIEF DESCRIPTION OF THE DRAWINGS

The accompanying drawings, which are incorporated herein and form part of the specification, illustrate the present invention and, together with the description, further serve to explain the principles of the invention and to enable a person skilled in the pertinent art to make and use the invention. In the drawings, like reference numbers indicate identical or functionally similar elements. Additionally, the left-most digit(s) of a reference number identifies the drawing in which the reference number first appears.

FIG. 8A shows an imaging device having an improved folding mirror according to one embodiment of the present invention;

FIG. 8B shows a close-up view of the improved folding mirror according to the present invention;

DETAILED DESCRIPTION OF THE EMBODIMENTS

1. Overview

Figure 1A:
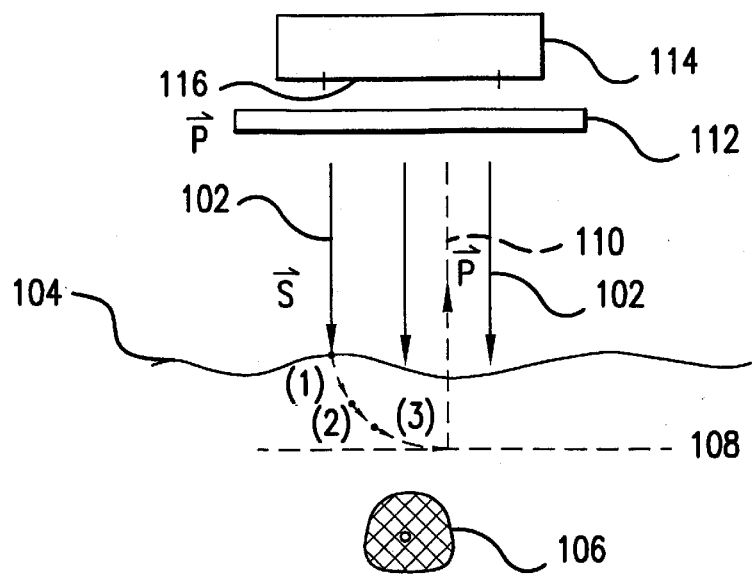
FIG. 1A depicts scattering events in the near field with standard reflectance spectrophotometry.

The present invention is directed to a method and apparatus for analysis, particularly non-invasive, in vivo analysis of a subject's vascular system. In particular, the device and method of the present invention provide a means for creating a virtual source of illumination from within the living tissue region surrounding a blood vessel or tissue area being imaged. As a result, the present invention uses transmission, rather than reflection, for the images that are analyzed.

2. Terminology

In order to form an image, two criteria must be met. First, there must be image contrast resulting from a difference in the optical properties, such as absorption, index of refraction, or scattering characteristics, between the subject to be imaged and its surroundings or background. Second, the light that is collected from the subject must reach an image capturing means without substantial scattering, i.e., the image should be captured from a depth that is less than the multiple scattering length. As used herein, "image" refers to any image that satisfies the foregoing two criteria. The resolution required for capturing the image is dictated by the spatial homogeneity of the imaged portion. For example, an image of individual cells requires high resolution. An image of large vessels can be done with low resolution. An image suitable for making a determination based on pallor requires very low resolution.

The tissue covering the imaged portion is thus preferably transparent to light, and relatively thin, such as the mucosal membrane on the inside of the lip of a human subject. As used herein, "light" refers generally to electromagnetic radiation of any wavelength, including the infrared, visible, and ultraviolet portions of the spectrum. A particularly preferred portion of the spectrum is that portion where there is relative transparency of tissue, such as in the visible and near-infrared wavelengths. It is to be understood that for the present invention, light can be coherent light or incoherent light, and illumination may be steady or in pulses of light.

The present invention utilizes an illumination technique to transform an illumination beam into a high contrast illumination pattern. This illumination pattern is one in which the illuminated region of the imaged plane falls entirely outside the field of view of an imaging system's objective. In a preferred embodiment, the illumination pattern has both a low intensity region (preferably in its central region) and a high intensity region (preferably in its outer region), where the high intensity region impacts the object plane outside the field of view of the imaging system's objective. An annulus or a ring of light is an example high contrast illumination pattern described herein.

The device of the present invention can be used for imaging and analysis of large vessels, small vessels, and capillary plasma. As used herein, "large vessel" refers to a vessel in the vascular system of sufficient size so that a plurality of red blood cells flow side-by-side through it. "Small vessel" refers to a vessel in the vascular system of a size so that red blood cells flow substantially "single file" through it.

To implement the method of the present invention, a light source is used to illuminate the region surrounding the portion of the subject's vascular system to be imaged, such as a blood vessel or tissue sample. The light emanating from the image is captured by an image capturing means. By image capturing means it is meant a device capable of capturing an image as defined herein. Suitable image capturing means include, but are not limited to, a camera, a film medium, a photosensitive detector, a photocell, a photodiode, or a charge coupled device (CCD) camera. An image correcting and analyzing means, such as a computer, is coupled to the image capturing means for carrying out image correction, scene segmentation, and blood characteristic analysis.

The "depth of penetration" or path length for illumination light is controlled by at least three parameters: (1) the wavelength of light; (2) the size and density of the particles with which the light interacts; and (3) the index of refraction. Normally, if the wavelength of light, the particle size and density, and the index of refraction are constant, then the depth of penetration is constant. Therefore, a measurement made per unit area in such an image is proportional to a measurement per unit volume because the depth of penetration is constant. An area measurement is a volume measurement with a constant third dimension (depth). Note that the depth of penetration can vary locally with tissue structure, based on the above parameters.

Crossed-polarizers are also preferably used in implementing the present invention. One polarizer is placed in the light path between the light source and the illuminated portion of the subject's vascular system. A second polarizer or "analyzer" is placed in the image light path between the illuminated portion and the image capturing means. The second polarizer has a plane of polarization substantially orthogonal to the plane of polarization of the first polarizer. The crossed-polarizer configuration improves the collection of light that has interacted with the illuminated portion of the subject's vascular system and tissue by eliminating light that has simply been reflected and has not fully interacted with the illuminated portion. Therefore, light with no information regarding the illuminated subject is eliminated. In this manner, the image contrast is vastly increased, thereby improving visualization in the illuminated portion.

3. Reflectance Spectrophotometry

As mentioned above, several conventional in vivo imaging devices have been developed based on reflectance spectrophotometry. Conventional reflectance spectrophotometric imaging devices are often based on Kohler-type illumination (see W. Smith, *Modem Optical Engineering*, McGraw-Hill, Inc., $2^{nd}$ Ed., especially p. 229 (1990), incorporated by reference herein). Kohler illumination comprises a light source which is imaged by a high numerical aperture condenser lens into an aperture stop of an objective lens. The illumination propagates through the objective to the object plane where it forms a uniform, featureless disk of illumination. This is due to the fact that this plane is the location of a pupil of the illumination system. Typically a polarizing beam splitter or a half silvered folding mirror is utilized to bring the illumination coincident with the imaging objective's optical axis. After being reflected off the beam splitter, the light from the illumination source propagates along the same optical path as the image forming light. The light from the illumination optics propagates towards a tissue region being viewed, while the image forming light is scattered from the tissue region and propagates out from it towards an image capturing means.

In order to provide high quality images, illuminating light, which is specularly reflected from intermediate optical surfaces due to Fresnel reflections can be extinguished from the imaging path by use of an analyzing crossed polarizer in front of the image capturing means. However, diffusely scattered light from, e.g., the walls of the lens housing and optical mounts, does not get completely extinguished. This is due to the fact that diffusely scattered light is randomly polarized, with 50% being aligned so as to pass through the analyzing polarizer in front of the image capturing means.

Another source of scatter originates in the living tissue region being viewed. Living tissue is highly scattering, structured, inhomogeneous and non-uniform. This non-uniformity in tissue structure leads to birefringence. The birefringent nature of tissue can interfere with the optimal performance of conventional in vivo imaging devices based on reflectance spectrophotometry. In these devices, the tissue covering the imaged portion must be traversed by light to obtain a reflected image without multiple scattering. The reflected image is then obtained from a single scattering of the reflected light. As such imaging devices that utilize crossed polarizers, such as the "bright field" imaging device described in co-pending and commonly assigned U.S. Pat. No. 5,983,120, issued Nov. 9, 1999 (referred to herein as the "'120 patent and incorporated by reference herein in its entirety), may still provide less than optimal image quality due to the birefringent nature of tissue. In addition, living tissue contains optically active substances such as glucose and collagen which cause a rotation of the polarization axis of incident light. The angle through which the polarization vector is rotated is a function of the length of propagation in the optically active tissue.

The light which is incident onto the tissue is scattered when it encounters diffuse surfaces and substances such as pigment in skin, hemoglobin in blood cells, cell nuclei, ligaments and muscles. Particularly suitable tissues are the mucosal membranes found in a variety of places in a human subject, such as the nose, mouth, conjunctivae, rectum, and vagina. Alternatively, for a premature baby, the skin itself is suitably transparent to light. The tissue under the tongue and in the area of the lip has less scattering and has more blood veins near the surface than most other parts of the body. Therefore the lip and the tissue region under the tongue are ideal areas for observing sub-surface vascular phenomena. Even in these areas, however, the depth to which sub surface observations can be made is limited due to the large amount of structure and inhomogeneous nature of tissue. It is generally difficult to image to depths larger than 400 micrometers ($\mu$m) in any tissue, even under the tongue or lip with any system.

When used for in-vivo imaging, the Kohler illumination system suffers from changes in contrast and changes in background illumination levels caused by rotation of the instrument with respect to the tissue region being viewed. The depth to which the instrument views or "sees" into the tissue varies with location and with orientation of the probe. These effects are caused by distributed polarization rotation caused by glucose, proteins and collagen and birefringence in the tissue. The on-axis nature of the illuminator also tends to allow "glare" light and direct, specular reflections back into the image capturing device.

Tissue is birefringent due to the fact that living cells are not symmetric, uniformly packed spheres or rectangles. Birefringence represents a net difference in refractive index in different directions. This is due to the differences in refractive indices of the cell walls, the cytoplasm and any interstitial liquids and the asymmetric nature of living cells. The effective refractive index is weighted by the length of propagation in the medium and the refractive index of each component as follows:

$$n_{eff} = \Sigma n_i * L_i / \Sigma L_i$$

where $n_i$=refractive index of $i^{th}$ component $L_i$=length of $i^{th}$ component Cellular structure varies throughout the body and locally in areas such as the underside of the tongue. Some areas have long thin muscle cells, which tend to be birefringent since the refractive index of the cell walls is different than that of the cytoplasm and the interstitial fluids. In one direction the electric field vector of the incident light is aligned with the long axis of the cell walls (and the effective refractive index is closer to the refractive index of the cell wall) whereas in the other direction the electric field vector spends a larger fraction of its time in the cytoplasm in the cell and the interstitial fluids as it propagates. The amount of birefringence varies as a function of position in the tissue since the cell structure varies with function. Birefringence can vary both the phase and the direction of the incident light.

Another factor that contributes to poor image quality is the propagation length dependent optical activity of certain biological molecules such as glucose, collagen and certain proteins. These biological molecules cause a rotation of the electric field vector which is proportional to the length of propagation in the media and to the concentration of the molecules. This length dependent polarization rotation allows some light which is subject to specular reflection from features inside the tissue (such as cell walls) to be transmitted through to the image plane, since at some depth of penetration the polarization vector of the incident light will be rotated by 90 degrees as it exits the tissue thereby allowing it to pass through the analyzing polarizer.

These two effects combine to allow some reflected light from arbitrary and varying depths within the tissue to propagate to a detector plane of the image capturing means without being scattered within the tissue. The variation of the amount of reflected light image and the depth from which it is reflected cause a change in contrast of the images which is directly related to the orientation of the probe.

According to the present invention, a system which is insensitive to instrument rotation and the angle of incidence of the illumination will be more accurate and provide more repeatable readings of any parameters being measured.

4. Scattering in Tissue

The interaction of light with matter is characterized by scattering theory. When an electromagnetic wave impinges on an atom or molecule it interacts with the bound electron cloud, imparting energy to the atom. The removal of energy from an incident wave (i.e., incident light) and the subsequent reemission of some portion of that energy is known as scattering. It is the underlying physical mechanism operative in reflection, refraction, and diffraction. For a general discussion of scattering, see Hecht and Zajac, *Optics*, 4th Ed., Addisson and Welsey (1979), especially Chapter 8 (incorporated by reference herein).

For example, reflected light can be characterized as having three distinct components. The first component is a "mirror or specular reflection" that preserves the image of the source in a reflection. The second component is a "rough surface scattering" component. The rough surface scattering component is scattered light that is scattered by a rough surface, and does not preserve the image of the source. However, both the mirror reflection component and the rough surface scattering component retain polarization. The third component is a "small particle scattering" component, commonly known as a "Rayleigh scattering" component. The Rayleigh scattering component is light that is scattered by particles that are small compared to the wavelength of the illuminated light. Rayleigh scattering de-polarizes light. Therefore, the Rayleigh scattering component is the only component of reflected light that is de-polarized so that the original polarization is lost. Typically, light must undergo more than one (usually at least three) scattering events to completely change polarization.

For in-vivo systems that utilize de-polarized light to form images, such as the device described in the '120 patent, the birefringent nature of tissue can lead to less than optimal images. FIG. 1A is a simplified illustration of how scattering from an optically active or birefringent tissue layer can interfere with the optical quality of an image. In this illustration, an imaging device is attempting to image a blood vessel of interest that is located within a tissue region underneath the skin of a subject. The blood vessel of interest is shown as a cross section of blood vessel or capillary 106. In this conventional reflectance-based system, the illuminating beam is directly incident on capillary 106 and is within the field of view 116 of a detector 114.

For example, an illumination source (not shown) provides a light beam, depicted by light ray 102, to illuminate capillary 106. Light ray 102 is polarized in the S direction. When light ray 102 impinges skin surface 104, one or several of the aforementioned scattering interactions may occur. For example, if light ray 102 is subject to a single specular reflection or rough surface scatter, the reflected ray will maintain its polarization in the S direction, and will be extinguished by analyzer 112, which only passes P polarized light. In other words, any S polarized light reflected off skin layer 104 will not reach detector 114.

If light ray 102 is not absorbed by or reflected off skin layer 104, the light ray 102 will likely undergo one or more scattering events within the tissue region. For example, FIG. 1A depicts the transmitted light ray undergoing three scattering events (events (1), (2), and (3)). As mentioned in the previous section, there may exist a layer within the tissue region that is weakly birefringent or diattenuative. This can be especially problematic if the subsurface birefringent layer, such as layer 108, is located between capillary 106 and detector 114. In other words, the birefringent layer is located in the near field, which is the region directly in front of the blood vessel of interest (e.g., capillary 106) that lies within the image path. In general, when polarized light passes through a birefringent material, the polarization vector is rotated through some angle $\Delta\phi$.

For purposes of this description, the image path is defined by the path originating at the blood vessel of interest and ending at the detector. Note also that for this example, collection optics, such as objective lenses are not depicted in FIG. 1A for simplicity. In this example, light ray 110, which is at least partially polarized in the P direction, will be reflected off layer 108, transmitted through analyzer 112, and detected by detector 114. This type of reflected light signal acts as "glare" and impacts the quality of the image obtained by detector 114.

According to the present invention, this type of spurious "glare" signal is greatly reduced (and image contrast greatly improved) if the blood vessel of interest is back-illuminated rather than directly illuminated. Further, according to the present invention, this back-illumination can be created by non-invasive means.

Figure 1B:
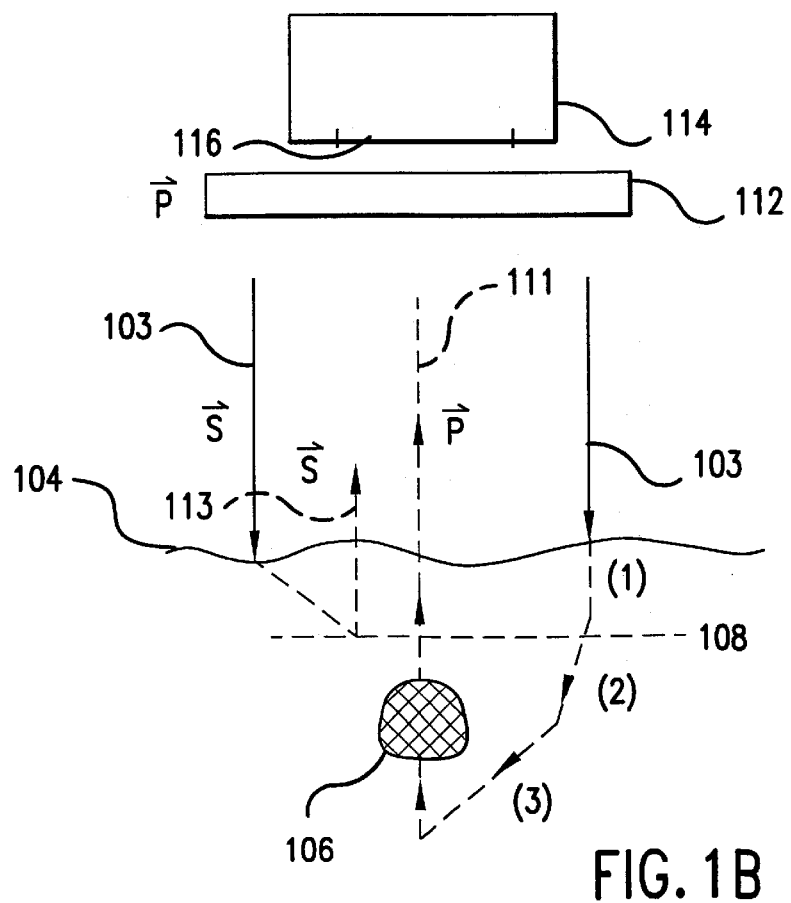
FIG. 1B depicts the illumination technique of the present invention.

FIG. 1B is a simplified illustration of how the method and device of the present invention creates a virtual source from deep within living tissue. In this manner, light diffuses through the blood vessel or tissue region of interest. The blood vessel is in turn effectively back-lit, providing maximum contrast of the image to the detector. Further, the amount of light emanating from the near field is greatly reduced.

FIG. 1B depicts an environment similar to FIG. 1A. One important change, however, is that the illuminating beam, characterized by light ray 103, is incident on skin surface 104 outside the field of view (FOV) 116 of detector 114. Moreover, the illuminating beam is not directly incident on capillary 106. Even if there is a birefringent layer 108 in the near field of the tissue region, it is unlikely that light scattered and reflected off layer 108 will become depolarized. This is shown by light ray 113.

Light ray 103, which is initially polarized in the S direction, is directed to a region outside the field of view of detector 114. As light passes through layer 108, it loses its pure S polarization, and gains a P polarization component. As it scatters more from deeper areas of the tissue region, the illuminating beam eventually becomes a random mix of S and P polarization. Thus, the illumination light can be scattered or reflected from deep within the tissue region (i.e., at a depth greater than the depth of the blood vessel being imaged). Eventually, a portion of this light, represented by light ray 111, is transmitted through capillary 106. The P polarization component of light ray 111 is transmitted by analyzer 112 and is captured by detector 114.

5. High Contrast Illumination Device and Method

The present invention is a device and method that provides a high efficiency illuminator for in-vivo investigations of the function of blood vessels and tissue. The ability to optically image deep into living tissue allows for applications such as the measurement of blood parameters, red and white blood cell counts, platelet counts, hemoglobin concentration, and the hematocrit.

The present invention utilizes an illumination technique that relays a maximum amount of illumination energy from a light source to an object plane in a manner such that clear images of sub-surface features can be obtained. The device of the present invention forms a high contrast illumination pattern, where the illumination is projected into a ring of light around the tissue region under test that is outside the field of view of a camera or CCD sensor (or its objective lens). Other illumination patterns, such as non-annular patterns, can also be utilized to image the tissue region under test as would be apparent to those of skill in the art given the present description.

The high contrast illumination pattern of the present invention can be created in several different ways. First, an obscuration can be placed in the illuminating beam path. Second, an optical element referred to as an "axicon" can be placed in the illuminating beam path. An axicon is an optical element that collects all of the light emanating from the light source and directs the light into a ring pattern in the far field. Third, in a similar manner, a conical diffraction grating or a hologram can also be utilized in place of the axicon.

Due to the multiple scattering events encountered by the illumination beam as it propagates through the tissue region under test, diffuse light from outside the field of view (FOV) of the image capturing means of the present invention will illuminate the tissue region under test (which is inside the FOV of the image capturing means). According to the present invention, the scattered illumination will be incident from above and below the area of interest since the scattering occurs throughout the illuminated volume. Therefore the image intensity distribution on the imaging means will have both scattered light which has been reflected off deeper layers (i.e., back-scattered) and transmitted through the blood vessels as well as scattered light reflected off the top surface of the blood vessels.

Also, using the device and method of the present invention, no reflected, unscattered light is incident onto the image capturing means because all directly reflected light is outside the FOV of the image capturing means and its corresponding objective and thus cannot be captured within the numerical aperture of the objective of the image capturing means.

6. Preferred Embodiments of the Present Invention

The present invention is described in terms of several example embodiments. Description in these terms is provided for convenience only. It is not intended that the invention be limited to application in these example embodiments. In fact, after reading the following description, it will become apparent to a person skilled in the relevant art(s) how to implement the present invention in alternative embodiments.

a. First Embodiment

The first embodiment of the present invention is a device (or in vivo apparatus) that provides a high contrast illumination pattern that is projected onto a tissue region of a subject in order to provide an image of blood vessels, blood flow, or tissue contained therein. The in vivo apparatus comprises a light source, an illumination system, and an imaging system. The imaging system includes an imaging detector and its objective.

The illumination system provides an illumination beam that is used to illuminate a particular blood vessel or tissue area (referred to as the "object") of a patient or subject. The illumination beam propagates along a path or segment referred to as the illumination path. The detector receives light emanating from the object. This light is also referred to as the image beam. The path or segment that the image beam travels is referred to as the image path. According to the present invention, the in vivo apparatus can be designed so that the illumination beam and the image beam share a common optical axis through a single objective, thus forming a coaxial system. Their axes can be combined using a beam splitter.

In a preferred embodiment, a linearly polarized, annular illumination source is projected onto the object plane of an imaging reflection spectrophotometer. It is necessary only that the extent of the projected source lie entirely outside the clear FOV of the image capturing means along the image path or segment of the in vivo apparatus. The annular light source can be produced by imaging a circular obscuration placed in the path of a Kohler illumination system. Since all incident light is exterior to the FOV, imaged light must come from deep within the tissue as discussed above in the Scattering Section. In a preferred embodiment, by utilizing crossed polarization in illumination and imaging, the image beam must come from multiple scattering events. The effect of this arrangement in this system is to produce true back-illumination: the light source is effectively moved to a region behind the object plane in a non invasive manner.

Figure 2:
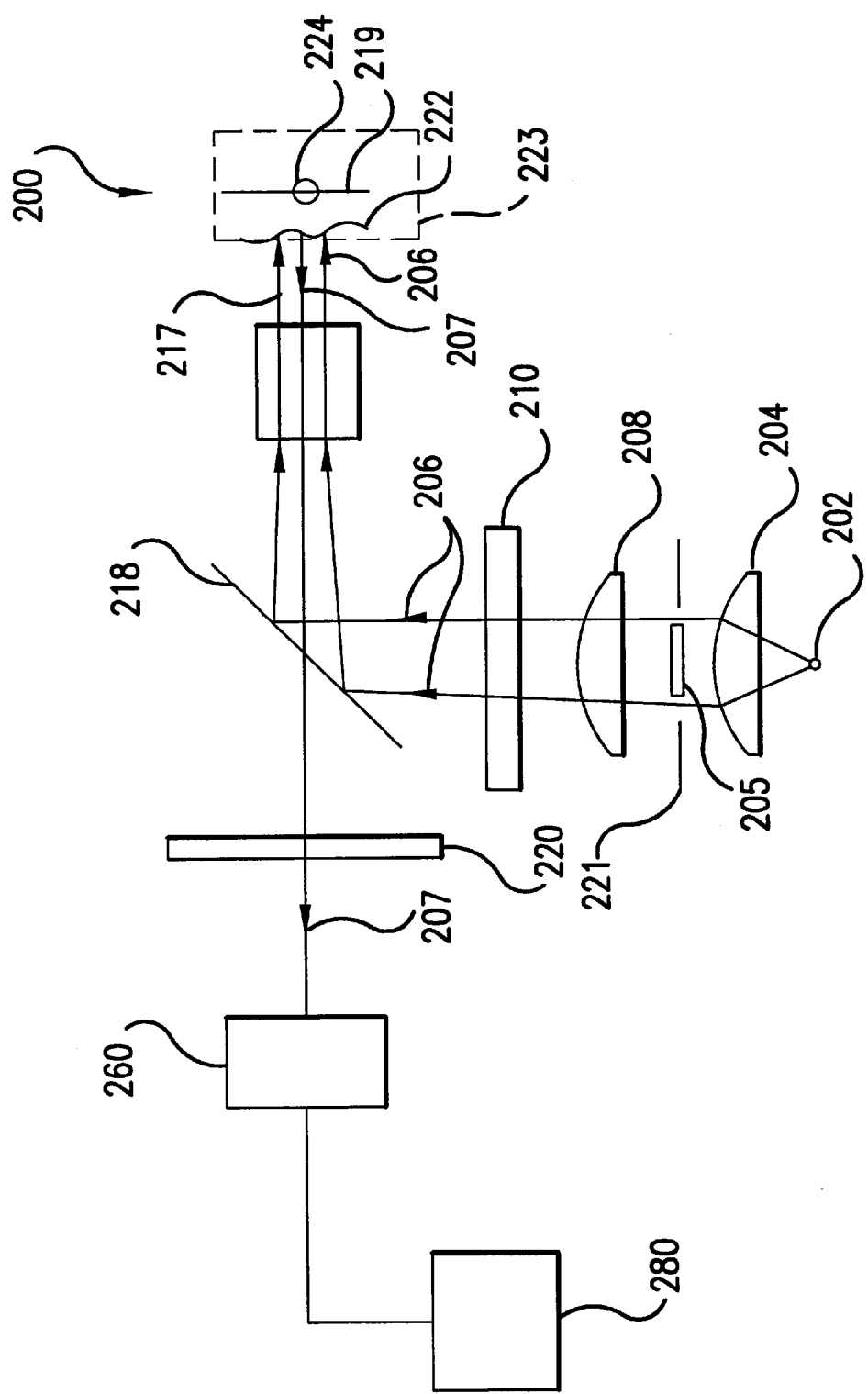
FIG. 2 shows an imaging device having an obscuration according to one embodiment of the present invention.

FIG. 2 shows a block diagram illustrating one embodiment of an apparatus 200 for non-invasive in vivo analysis of a subject's vascular system. Apparatus 200 includes a light source 202, a relay lens 208, a detector 260, and an objective 217.

Light source 202 illuminates a tissue region of a subject (shown generally at 223). Although one light source is shown in FIG. 2, it is to be understood that the present invention is not limited to the use of one light source, and more than one light source can be used. In an embodiment where more than one light source is used, each light source can be monochromatic or polychromatic. Light source 202 can be a light capable of being pulsed, a non-pulsed light source providing continuous light, or one capable of either type of operation. Light source 202, can include, for example, a pulsed xenon arc light or lamp, a mercury arc light or lamp, a halogen light or lamp, a tungsten light or lamp, a laser, a laser diode, or a light emitting diode (LED). Light source 202 can be a source for coherent light, or a source for incoherent light.

Light source 202 is collimated by a collimating lens or condenser 204. The optical and physical characteristics of collimating lens 204 depend on the type of light source being used and the type of image to be eventually projected onto an object 224. The optical characteristics of collimating lens 204 include its focal length, numerical aperture, and f-number (f/#). The physical characteristics of collimating lens 204 include its material type (glass, plastic, etc.) and shape. Suitable parameters will be apparent to one of skill in the art based on the present description.

For example, if a halogen lamp is used as light source 202, collimating lens 204 can comprise a spherical F1 lens with a focal length on the order of 5 millimeters (mm). The lens can be made out of standard BK7 glass, which is transparent in the visible region of the electromagnetic spectrum. In addition, if a lamp is used as light source 202, a retro reflector (not shown) can be utilized to collect and reflect light emanating out to the rear portion of the lamp towards collimating lens 204.

According to this embodiment of the invention (also referred to herein as the "obscuration embodiment"), a high contrast illumination pattern is projected onto object 224 as follows. An obscuration 205 is placed in the illumination path to transform the illumination emanating from light source 202 into a high contrast illumination pattern. The illumination path, represented here as path 206, is the path of light originating at light source 102 and continuing on to object 224.

In a preferred embodiment, obscuration 205 is located at aperture or stop 221. In this embodiment, a circular obscuration is utilized. Obscuration 205 blocks a predetermined portion of the incident illumination beam. The portion of the illumination beam not blocked by obscuration 205 continues to propagate along the illumination path. The remaining illumination beam 206 resembles an annulus or ring of light with a dark central region. This pattern has its darkest spot (i.e., lowest intensity) in its central region and highest intensity near the edges of the pattern. Other suitable types of obscurations, including non circular obscurations, will be apparent to those of skill in the art given the present description.

A lens 208 (also referred to as relay lens 208) projects the high contrast illumination pattern onto an object plane 219. The object plane herein is the plane that is perpendicular to the image path, shown here as path 207, where the object 224 is located. In FIG. 2, the object plane is illustrated by plane 219. In a preferred embodiment, the optical parameters defining projection lens 208 can be chosen in accordance with those utilized in a Kohler illumination system. In Kohler illumination, the source aperture (here, stop 221) is imaged or projected onto the object plane. In this embodiment of the present invention, since stop 221 is projected onto object plane 219, the high contrast illumination pattern is also projected onto the object plane.

Figure 3:
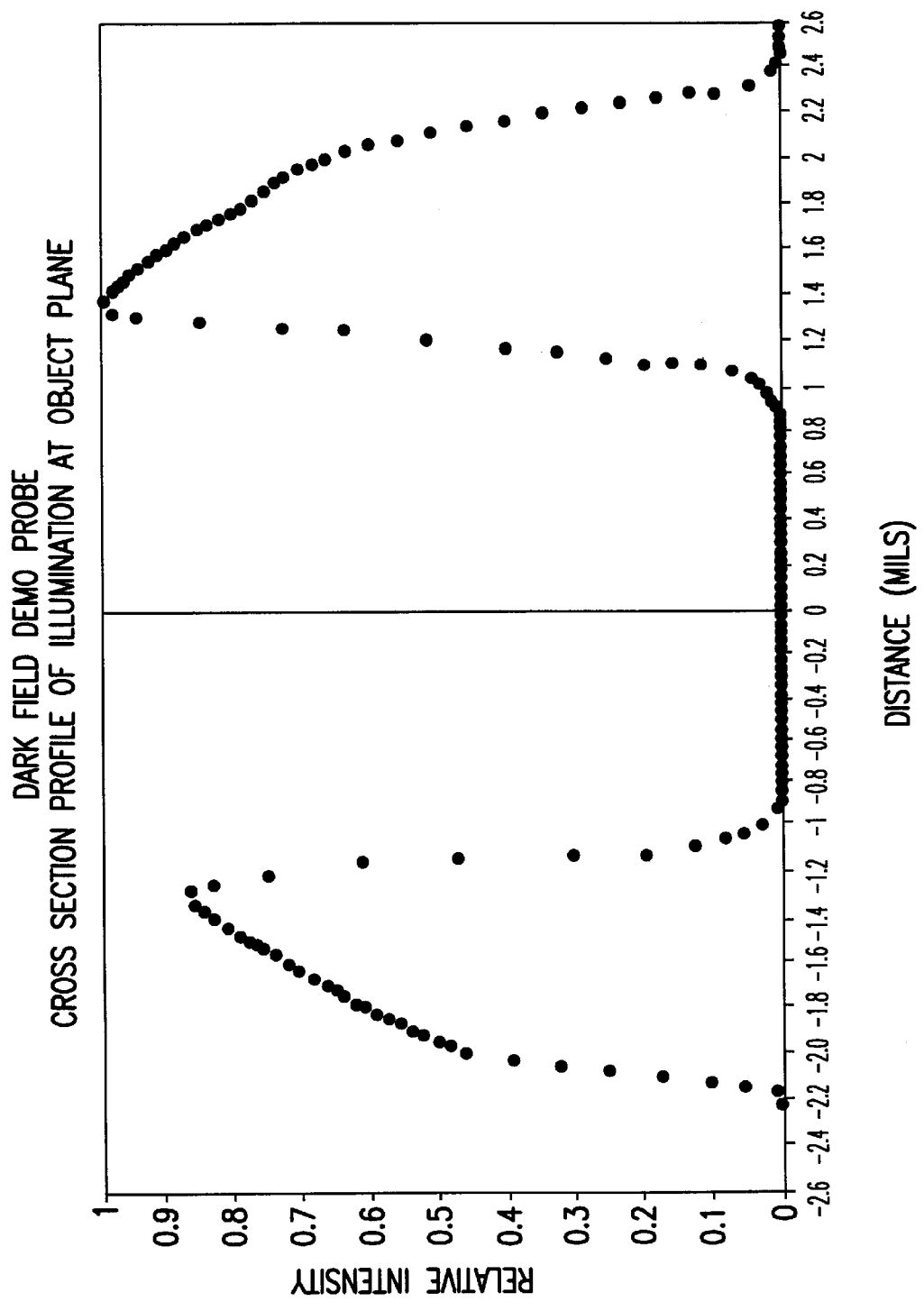
FIG. 3 shows a cross-section profile of illumination at the object plane according to one embodiment of the present invention.

In apparatus 200, projection lens 208 is designed to image the high contrast illumination pattern onto object plane 219 and to image light source 202 at the objective of the imaging system, here shown as objective 217. Thus, in a preferred embodiment, apparatus 200 provides that a collimated ring of light is incident on skin surface 222. For example, FIG. 3 shows a measured illumination profile for an example illumination pattern projected onto an object plane. The illumination profile plots the relative intensity of the illumination signal as a function of distance from the image axis. Thus, the high contrast illumination pattern of this embodiment has its lowest intensity in the middle and highest intensity near the edges of the pattern. For example, the device of the present invention produces a figure of merit of about 400 to 1. This figure of merit represents the ratio of illumination intensity of the outer portion of the annular pattern as compared to the dark spot in the central region.

Referring back to FIG. 2, a folding mirror or beam splitter 218 is used to form a light path between light source 202 and subject 224. According to one embodiment of the present invention, beam splitter 218 is a coated plate having 50% reflection of illumination beam 206. Other embodiments of beam splitter 218 are discussed below.

In a preferred embodiment, a first polarizer 210 can placed between light source 202 and subject 224. First polarizer 210 polarizes light from light source 202. A second polarizer or analyzer 220 can be placed between object 224 and image capturing means 260 along image path 207. Polarizers 210 and 220 preferably have planes of polarization oriented substantially orthogonal (or 90°) relative to each other. Polarizers, such as polarizers 210 and 220, having planes of polarization oriented 90° relative to each other are referred to herein as "crossed-polarizers".

As mentioned above, when polarized light passes through a birefringent material, the polarization vector is rotated through some angle $\Delta\phi$. In a crossed-polarizer system, such as described in this preferred embodiment, the change in intensity is proportional to $\cos^2(\Delta\phi)$.

The efficiency of a polarizer is a function of the percentage of the input light that is transmitted through the polarizer. For each unit of unpolarized (randomly polarized) light input to a polarizer, a perfectly efficient polarizer would transmit out 50% of the inputted light. When randomly polarized light is input to two perfect polarizers (regardless of efficiency) configured as cross-polarizer, all light is extinguished, i.e., no light is transmitted through the second polarizer. The more light that is extinguished by cross-polarizers (i.e., the less randomly polarized light that is transmitted through the cross-polarizers), the greater the extinction of the cross-polarizers. Cross-polarizers having an extinction coefficient of at least $10^{-3}$ (for each unit of randomly polarized light input into the cross-polarizers, $\frac{1}{1000}$ is transmitted through the cross-polarizers) are suitable for use with the present invention. Suitable cross-polarizers are available as sheet polarizers from Polaroid Corp., Massachusetts.

In one embodiment of the present invention, light source 202 is itself a source of polarized light, for example, a laser or a laser diode, so that a separate first polarizer 210 is not required. Second polarizer 220 has a plane of polarization oriented 90° relative to the plane of polarization of polarized light source 202.

In another embodiment, beam splitter 218 is a polarizing beam splitter. For example, in this embodiment, a polarizing beam splitter cube is used in conjunction with a linear polarizer in the source. A polarizing beam splitter cube transmits nearly all of one polarization and reflects nearly all of the polarization oriented at 90 degrees to it. Polarizing beam splitters are known in the art and can be purchased from many commercial optics vendors. This polarizing beam splitter can be aligned to ensure that all light incident on the beam splitter cube is the same polarization that will be reflected. This minimizes stray light in the apparatus, which would pass through the beam splitter cube, and ultimately degrade the signal to noise figure of the captured image. However, the selectivity of the polarizing beam splitter cube is a function of the angle of incidence of the light on the interface and on the numerical aperture of the optics. As the illuminating beam converges or diverges, the reflectance of the beam splitter over the full aperture decreases. Similarly as the field angle increases the reflectivity encountered by the off-axis portions of the beam also decreases.

Preferably, the image from object 224 emanates from a depth less than a multiple scattering length and travels along image path 207 to image capturing means 260. However, the imaging system of the present invention can also capture images formed from a depth greater than a multiple scattering length. Objective 217 is used to magnify the image of object 224 onto image capturing means 260. Objective 217 is placed co-axially in illumination path 206 and image path 207. Image capturing means 260 is located in a magnified image plane of objective 217. Objective 217 can comprise one or more optical elements or lenses, depending on the space and imaging requirements of apparatus 200, as will be apparent to one of skill in the art based on the present description.

Suitable image capturing means 260 include those devices capable of capturing a high resolution image as defined above. The image capturing means captures all or part of an image for purpose of analysis. Suitable image capturing means include, but are not limited to, a camera, a film medium, a photosensitive detector, a photocell, a photodiode, a photodetector, or a charge coupled device camera. For example, video cameras and charge coupled device (CCD) cameras having a 640×480 pixel resolution and 300 Hz framing rate can be used. A particularly preferred image capturing means is a Sony ICXL model CCD camera.

Image capturing means 260 can be coupled to an image correcting and analyzing means 280 for carrying out image correction and analysis (explained below in the image analysis section). The resolution required for the image capturing means can depend upon the type of measurement and analysis being performed by the in vivo apparatus. For example, the image resolution required for determining the hemoglobin concentration (Hb) is lower than the image resolution required for making cellular measurements, such as MCV or cell counts. For example, hemoglobin concentration measurements can be carried out using photocells, such as one red filtered photocell and one green filtered photocell, as the image capturing means.

Preferably, objective 217 can be one or more lenses that are selected with the lowest magnification level required to visualize the illuminated object. The magnification required is a function of the size of the object in the illuminated tissue to be visualized, along with the size of the pixels used for the image. For example, low magnification provides a high depth of field, but more crudeness to the image. High magnification provides a low depth of field, but is more susceptible to blurring caused by motion. Blood vessels in the microvascular system are typically 10–40 micrometers ($\mu$m) in diameter. Ten to twenty (10–20) pixels per blood vessel diameter provide a suitable image with a 10×lens. Lower magnification could be used with pixels of smaller size.

As mentioned above, according to a preferred embodiment, illumination path 206 and image path 207 share a common axis. This coaxial nature allows for objective 217 to be utilized for more than one purpose. First, objective 217 acts as the objective for image capturing means 260. In other words, it collects the image beam emanating from object 224 onto image capturing means 260. Second, objective 217 acts to focus the high contrast illumination pattern onto the object plane. As mentioned above, the high intensity portion of illumination beam 206 is directed outside the FOV of the image capturing means 260.

The combination of the optical characteristics of objective 217 and image capturing means 260 determine the FOV of device 200. The FOV of the image capturing means can be limited by many parameters including the numerical aperture of its objective (here objective 217), entrance pupils, exit pupils, and the area of the detector comprising image capturing means 260.

Objective 217 can comprise a single lens or multiple lenses. The physical and optical parameters of objective 217 (e.g., lens material, numerical aperture, focal length, etc.) can be chosen according to the imaging parameters desired. Standard objectives are available from most commercial optics vendors, including Melles Griot and Newport Corp., both of California. The specific optical and physical characteristics of objective 217 will be apparent to those of ordinary skill in the art given the present description.

In another embodiment, image separating means, such as a second beam splitter (not shown) can be used to separate the image from object 224 into two or more image portions. Each image portion can be captured by a respective image capturing means, such as image capturing means 260. In addition, a spectral selection means, such as a grating, filter, and/or monochromator (not shown), can also be placed in image path 207 between second polarizer 220 and image capturing means 260. The spectral selection means can be, for example, a monochromator, a spectral filter, prism, or grating. For example, if hemoglobin concentration is to be determined, then a spectral selection means is preferably centered at about 550 nanometers (nm). As another example, if bilirubin concentration is to be determined, then a spectral selection means is preferably centered at about 450 nm.

Image capturing means 260 is coupled to image correcting and analyzing means 280 in a conventional manner. Image correcting and analyzing means 280 can be a computer or other type of processing. Image correcting and analyzing means 280 can be configured to carry out image correcting steps through hardware, software, or a combination of hardware and software. These image correcting steps will be described in detail below.

In yet a further embodiment, light source 202 is configured as a plurality of LED's, each LED emitting a different wavelength of light. For example, three LED's can be used to provide a source of green, blue, and red light. Use of a light source 202 that is configured to emit a particular wavelength or wavelengths of light, such as by means of one or more LED's, can eliminate the need for separate spectral selection means. A single image capturing means 260 can be used to capture the image from each of the three LED's. For example, a single color camera sensitive to multiple wavelengths (green, blue, and red) can be used to capture the image from each of the three (green, blue, and red) LED's.

In a further embodiment of the present invention, a light source can be optically coupled to a light pipe, a single optical fiber, or an optical fiber bundle (not shown). Various light pipes and optical fibers are well known in the art and are available from many commercial optics vendors. For example, a first end of a light pipe (i.e., the proximal or input end) can receive light emitted from the light source. The second end of the light pipe (i.e., the distal or output end) can be placed at the entrance pupil of the imaging device, such as stop 221. In this embodiment, an obscuration, such as obscuration 205, is designed so that its diameter is less than the outer diameter of the light pipe, thus creating a high contrast illumination pattern to be projected onto the object plane. Other implementations of fiber coupled light sources will be apparent to those of skill in the art given the present description.

b. Second Embodiment

According to a second embodiment of the present invention, the illumination of the tissue region being viewed can be provided in a more efficient manner. For example, device 200 shown in FIG. 2 projects a high contrast illumination pattern onto the tissue region being viewed, thus providing a low rotational effect due to near field tissue birefringence. Yet, apparatus 200 requires a substantial amount of power from light source 202. High output intensity may be needed in order to provide enough illumination to saturate the annular ring outside the FOV of detector 260, which yields enough light into the limiting numerical aperture of the objective lens of the detector. A relatively higher amount of power is required because about 50% of the collimated illumination beam collected by collimating lens 204 is blocked off by obscuration 205.

For example, assume that illumination source 202 is a tungsten filament, which is a semi-lambertian emitter. Lambertian emitters have a radiant exitance distribution which varies as the cosine of the angle from the surface normal. Therefore, obscuring the light emitted on the axis of the collimating lens (or condenser) greatly reduces radiant power which is incident at the object plane. The amount of attenuation is greater than the ratio of the obscured area to the total area of the illuminating beam. The amount of light (Transmission or "T") that is lost to an obscuration relative to the unobscured value can be determined by evaluating the following equation:

$$T = \frac{\int_0^\beta \cos(\theta)\,d\theta}{\int_0^\alpha \cos(\theta)\,d\theta}$$

$T=\sin(\beta)-\sin(\alpha)$ where $\beta=\tan^{-1}(r_1/f)$ $\alpha=\tan^{-1}(r_0/f)$ $r_1$=radius of lens clear aperture
$r_0$=radius of obscuration
f=distance from condenser to obscuration For example, if the clear aperture of the collimating lens has an angular subtense of 30 degrees from the source and the obscuration has an angular subtense of 14.5 degrees from the source, then the ratio of the areas of the clear aperture to the obscuration diameter is 40% while the fraction of emitted intensity lost is about 50%. For example, a device similar to that shown in FIG. 2 (i.e., including an obscuration) was modeled. The model device couples about 38% of the light emitted on axis and 28% from the off-axis points to the object plane.

According to a second embodiment of the present invention, substantially all of the illumination collected by the condenser from a small source can be redistributed into an annular pattern or ring of light at an intermediate image plane, thus transforming the illumination into a high contrast illumination pattern. This "unobscured" ring of illumination is then demagnified and imaged onto the object plane by the objective lens. This embodiment of the present invention eliminates the need to obscure a portion of the collimated illumination. Thus, no illumination from the source is wasted. Further, the change in image contrast due to probe angular orientation and relative alignment to the surface is minimized.

According to this embodiment, the redistribution of the light source intensity can be accomplished through the use of an axicon, a conical grating (a fixed period, blazed, diffractive gating), or a computer generated hologram.

Figure 4:
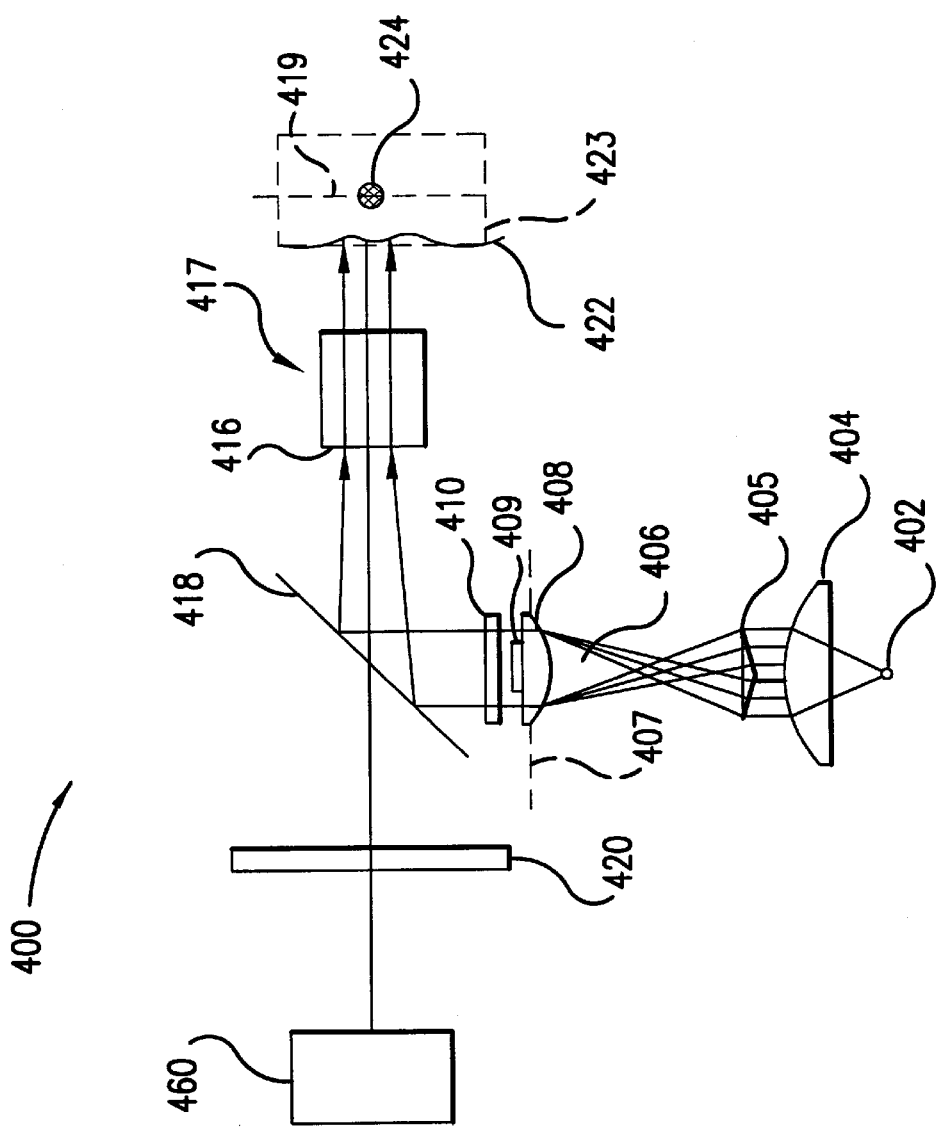
FIG. 4 shows an imaging device having a conical lens according to one embodiment of the present invention.

FIG. 4 shows a block diagram of this embodiment (also referred to herein as the "axicon embodiment") of an imaging apparatus 400. Imaging apparatus 400 comprises an illumination system and an imaging system. The illumination system includes a light source 402, a conical lens, here shown as an axicon 405, a relay or field lens 408 and a polarizer 410. The imaging system includes an image capturing means 460 and an objective 417.

Light source 402 illuminates a tissue region of a subject (shown generally as region 423). Similar to light source 202 (described above with respect to FIG. 2), light source 402 can include, for example, a pulsed xenon arc light or lamp, a mercury arc light or lamp, a halogen light or lamp, a tungsten light or lamp, a laser, a laser diode, or a light emitting diode (LED). A collimating lens or condenser 404 collects and collimates the illumination beam emanating from light source 402 in a similar manner to that described above for collimating lens 202 in FIG. 2. The illumination beam propagates to a tissue region 423 along an illumination path 406.

Instead of blocking a portion of the illumination beam with an obscuration, apparatus 400 utilizes an optical element referred to as an "axicon" to generate a high contrast illumination pattern that is projected onto tissue region 423. An axicon is a cone shaped optical element (also referred to as a conical lens) with a fixed apex angle which is symmetric about 360 degrees. This unique shape allows axicon 405 to produce an annular pattern (or ring of light) in the far field, such as at tissue region 423.

Figure 5A:
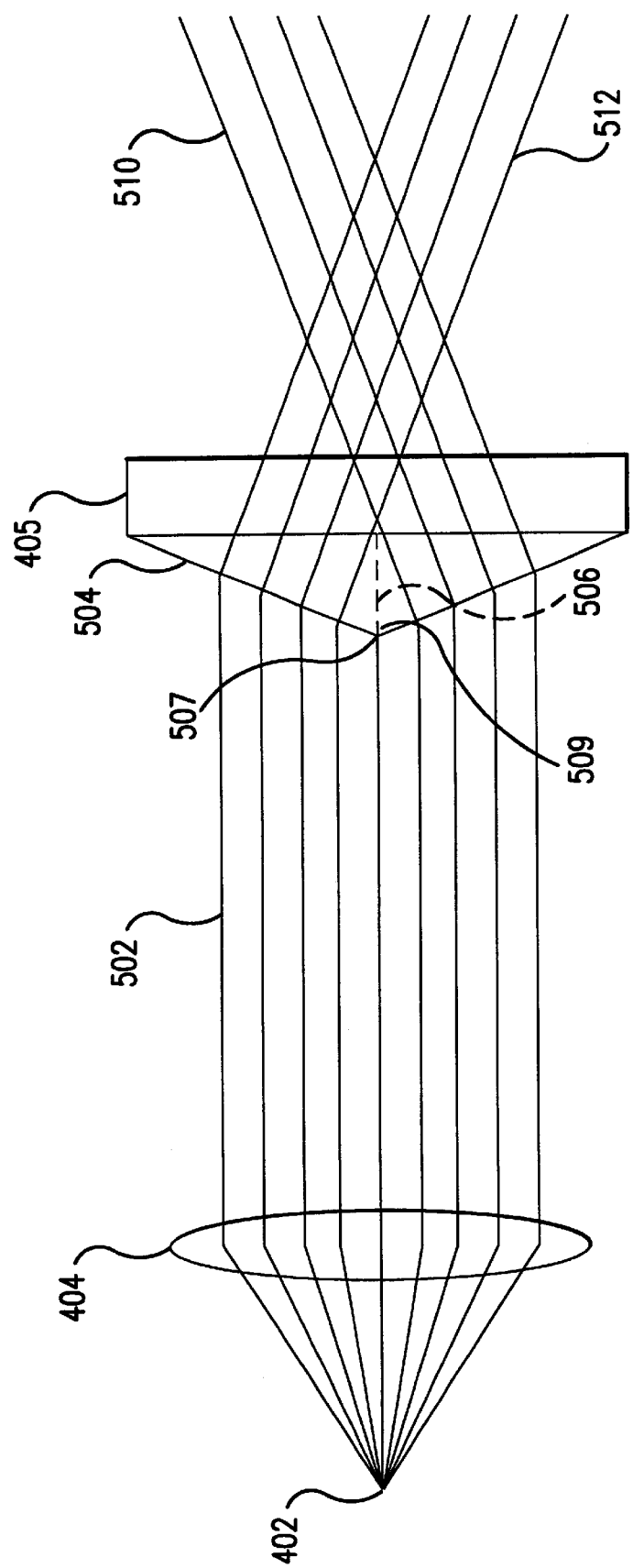
FIG. 5A shows a detailed view of an axicon.

FIG. 5A shows a detailed view of axicon 405. A collimated beam of light 502 is incident upon surface 504 (here, the entrance surface). The direction of propagation of beam 502 is normal to exit surface 508. The beam is refracted about the axicon's conic axis 506. Unlike a typical curved lens, axicon entrance surface 504 comes to a point at an apex 507. This pointed apex causes the exit beam, shown here as beams 510 and 512, to emerge at a constant angle. The angle by which the beam exits axicon 405 is proportional to an apex angle 509 and can be determined according to Snell's law. Moreover, only a minimal portion (about 1% or less) of the transmitted beam propagates parallel to the conic axis 506.

An annular pattern or ring of light is formed at relay lens 408 by the combination of axicon 405 and a collimator lens, such as condenser 404. The position of the collimator lens is preferably located such that the light incident on it is focused at infinity. Therefore, light from an on axis point generally emerges from the collimator lens in parallel and propagates towards infinity with little or no change in diameter of the beam. This light can be incident onto axicon 405 and then focused with an additional lens. In a preferred embodiment, condenser 404 is focused at relay lens 408 and axicon 405 is inserted in front of it. The focused image is then in the form of a ring of light at the relay lens. This ring of light can then be re-imaged by the objective lens, such as objective 417, to the object plane, where it forms a smaller ring of light with a dark central region.

In a preferred embodiment, the outer diameter of axicon 405 is large enough to receive the entire collimated illumination beam. An axicon, such as axicon 405, can be a glass molded or plastic molded element. Axicons are straightforward to manufacture and fairly simple to align. Axicons are available from several commercial lens vendors, such as Optics for Research, of New Jersey. Note that the choice of entrance and exit surfaces is for description purposes only: a light beam can be incident on either surface 504 or surface 508 and be refracted in a similar manner.

Alternatively, according to this embodiment of the present invention, a conical grating or a computer generated hologram (i.e., a holographic conical grating) can be used in place of axicon 405 to achieve the same desired illumination pattern at the tissue region. A conical grating is a fixed period, blazed, diffractive gating. Conical gratings are known in the art. Conical gratings can be used as alignment fixtures and to generate a diffraction free propagation beam.

Figure 5C:
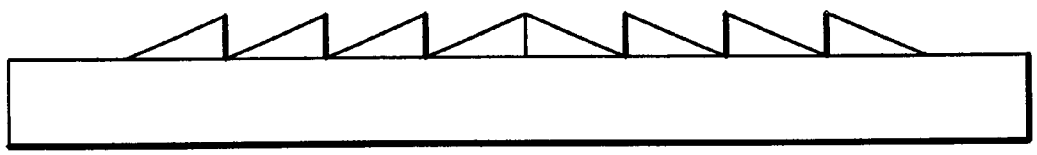
FIG. 5B shows a detailed view of a conical diffraction grating.
Figure 5B:
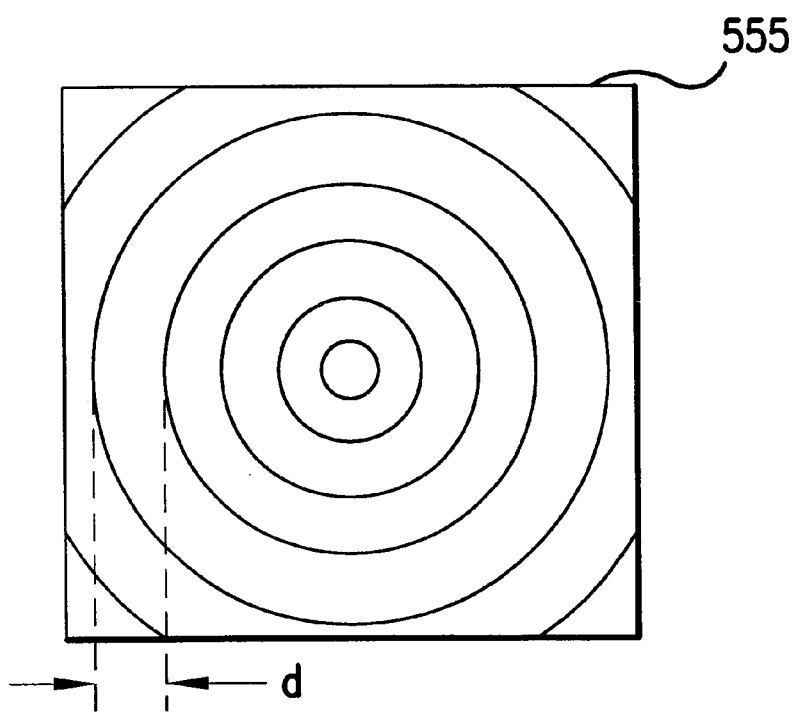

For example, a front view of a conical grating 555 is depicted in FIG. 5B. Preferably, conical grating 555 has rings of equal spacing, shown by spacing distance d, thereby forming a "bullseye" pattern on the front surface of conical grating 555. A corresponding side view of conical grating 555 is shown in FIG. 5C, which shows the conical grating having a diffractive surface profile. As a light beam is normally incident upon the grating, the light beam is diffracted at a constant exit angle. The exit angle of the transmitted beam is proportional to the wavelength of the incident light, the spacing distance d, and the angle of incidence of the light beam. After encountering a conical grating, only a minimal portion of the incident beam is transmitted parallel to its optic axis.

A conical grating, with a user specified spacing pattern, can be made from glass or plastic elements according to known photoresist or injection molding methods. For example, gratings can be formed in photoresist from interference patterns recorded from a combination of two or more laser beams. The diffractive features are then coated with a metal, such as nickel for use in molding. Alternatively, a metal master can be precision machined using known diamond turning technology. These metal masters can then be used as mold surfaces for injection or compression molding of plastics.

Further, an optical element having a hologram (also referred to as a holographic conical grating) can also be utilized to achieve a similar effect. The hologram is an emulsion film-based product that is coated onto a glass (or other suitable material) substrate. Methods of forming a hologram are known in the art. For example, holographic conical gratings are generally made by recording interference patterns generated by the combination of two or more laser beams, where these patterns are recorded as master gratings. Production versions can be formed as master gratings or be copied from master holograms. When used in the illumination system of the present invention, the combination of a conical grating and a field lens or a holographic conical grating and a field lens projects an annular pattern in the far field.

With respect to the present invention, a conical grating or holographic element can be placed in the illumination path, such as illumination path 406 of FIG. 4. For example, conical grating 555 can be placed in the illumination path, such as at the stop of a Kohler illumination system. A properly designed conical grating placed at a similar location to that of axicon 405 diffracts the collimated illumination beam in a similar manner to that shown in FIG. 4. The optical and physical parameters of conical grating 555 or a holographic element will be apparent to those of skill in the art based on the present description.

Figure 6:
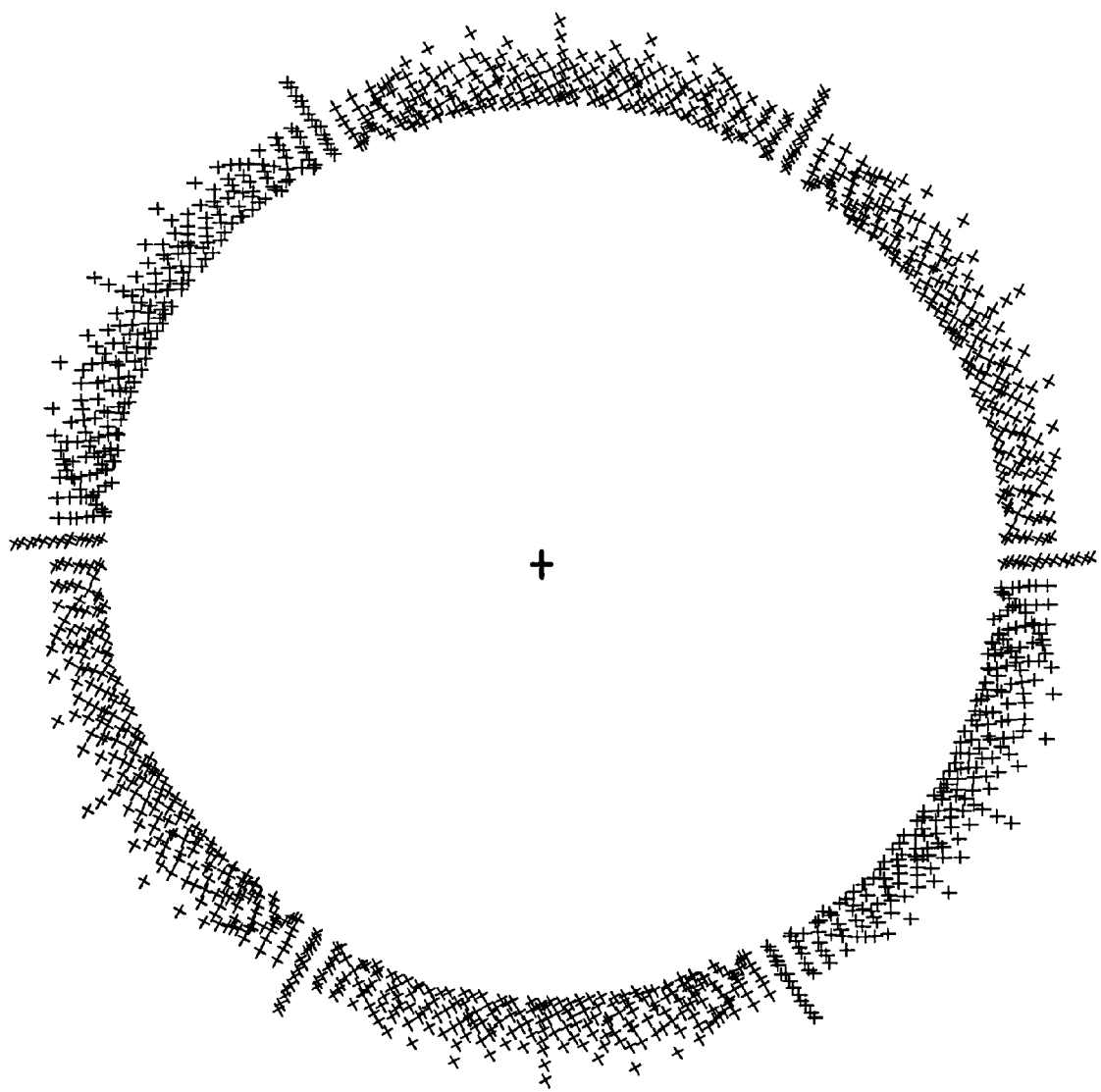
FIG. 6 shows an annular image pattern at the surface of a field lens.

Returning to FIG. 4, projection or field lens 408 is used to collect and project the imaged annular pattern onto tissue region 423, at a capillary 424. Field lens 408 can be placed along illumination path 406 at an intermediate image plane 407. When a lamp having a filament is utilized as light source 402, placement of field lens 408 at intermediate image plane 407 can prevent vignetting and the resultant loss of light for off axis points on the lamp filament by bending the off-axis rays towards the optical axis so they pass within the clear aperture of objective 417. FIG. 6 depicts an annular image pattern at the surface of a field lens, such as field lens 408.

As a representative example, the illumination system comprises a light source, a collimating lens, and an axicon. The axicon has a 6 millimeter (mm) diameter, with a surface sag of about 0.75 mm, and an apex angle of about 13 degrees. The field lens has a diameter of about 10 mm. This results in an annular pattern being incident on the object plane having a diameter of about 1.8 mm.

Preferably, the focal length of field lens 408 is chosen to image the exit pupil of the axicon onto the aperture stop (not shown) of objective 417. This configuration couples most or all of the light collected by condenser 404 onto object plane 419. The imaging system of apparatus 400 operates in a similar manner to that described above with reference to FIG. 2. Overall, if the exit face of axicon 405 and an entrance pupil 416 of objective 417 are the same size, and the filament is small enough (e.g., about 1 mm in length), apparatus 400 can provide as much as 2.5 times more light to tissue region 423 than apparatus 200. It is important to note that if a lamp is used as light source 402, there is a greater chance that the collimated illumination beam may enter axicon 405 at an angle. The resulting illumination beam would be off-axis with respect to optic axis 406. In turn, the intensity transmitted through axicon 405 and reaching the object plane may be reduced by as much as 50%. This "off-axis" illumination is a tradeoff to consider when using a lamp as the light source, which could lead to the annular illumination pattern being slightly off center (or slightly truncated). Thus, care should be excercised when collimating light source 402. Alternatively, if a laser or LED is used as light source 402, the alignment is more straightforward since the emitted light emanates from a substantially single point (i.e., a point source).

In a preferred embodiment, an obscuration 409 can also be utilized to minimize any on-axis illumination beam transmitted through axicon 405 from reaching tissue region 423 that is within the FOV of image capturing means 460. According to this embodiment, obscuration 409 is placed in the illumination path between field lens 408 and tissue region 423. Since the intensity pattern at the relay lens is in the form of a ring with a dark center, an obscuration can be placed in the center of the relay lens without blocking the desired illumination pattern. Thus, only aberrant and stray light will be blocked.

For example, as shown in FIG. 4, obscuration 409 is placed just after field lens 408. The outer diameter of obscuration 409 is less than the inner diameter of the annular illumination pattern. Preferably, the diameter of obscuration 409 can be the same size as the FOV of the image capturing means 460. In this manner, all of the annular pattern will reach tissue region 423 outside the FOV of detector 406. Any light transmitted through the apex of axicon 405 along optical axis 406 will be blocked by obscuration 409, thus further improving the image contrast viewed by detector 460. Other means of blocking any on-axis illumination will be apparent to those of skill in the art given the present description.

Figure 7:
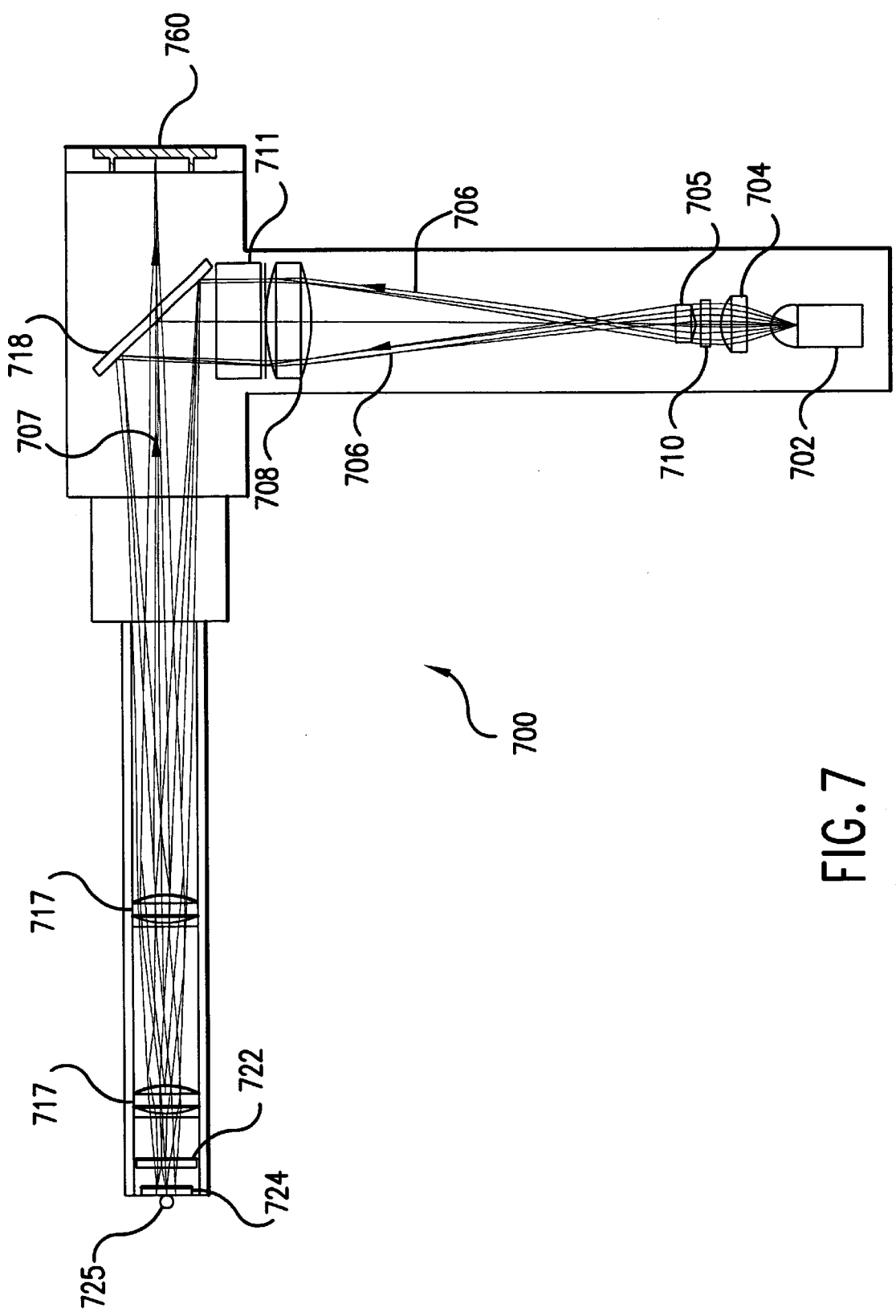
FIG. 7 shows a ray trace of an illumination beam and an image beam according to one embodiment of the present invention.

FIG. 7 depicts a model ray trace of the illumination and image beams for an experimental device 700. Similar to device 400 shown in FIG. 4, device 700 comprises a light source 702, a condenser 704, an axicon 705, a field lens 708, a beam splitter 718, an objective 717, and an image capturing means 760. Illumination emanating from light source 702 is collimated by condenser 702 and then polarized by a polarizer 710. Axicon 705 diffracts the illumination beam in a similar manner to that described above with reference to FIG. 4 for axicon 405. In this example, axicon 705 has a conic constant of about −19.0. The diffracted illumination beam, represented by light rays 706, is collimated by field lens 708. The illumination beam is redirected off beam splitter 718 through objective 717 onto an object plane (not shown), that is located just beneath the skin surface through which the beam is projected. The illumination beam has the general appearance of a ring of light, similar to the pattern shown in FIG. 6. The combination of field lens 708 and objective 717 also act to focus the annular ring of illumination. However, according to the present invention, the illumination beam can be focused onto an exit window 724, which corresponds to the skin surface, outside the field of view of image capturing means 760.

For a preferred embodiment of the present invention, an example optical formula sheet (or optical prescription) corresponding to the ray trace and the device of FIG. 7 is listed below in Table 1. Note that the optical characteristics of each surface encountered by the illumination beam are listed below in Table 1.

TABLE 1

| Surface # | Radius | Thickness | Glass | Conic Constant |
|---|---|---|---|---|
| Object (702) | Infinity | 4.7 | | |
| 1 Condenser (704) | Infinity | 2.5 | SF11 | |
| 2 | −4.71 | 1.0 | | |
| 3 Polarizer (710) | Infinity | 1.0 | BK7 | |
| 4 | Infinity | 0.5 | | |
| 5 Axicon (705) | $5 \times 10^{-10}$ | 2.0 | BK7 | −19.0 |
| 6 | Infinity | 37.54 | | |
| 7 Field Lens (708) | 39.45 | 4.0 | BK7 | |
| 8 | −18.20 | 0.5 | | |
| 9 Spectral Filter (711) | Infinity | 4.33 | BK7 | |
| 10 | Infinity | 6.0 | | |
| 11 Beam splitter (718) | Infinity | 60.0 | Mirror | |
| 12 Objective (717) | 18.11 | 2.3 | BK7 | |
| 13 | −13.51 | 0.9 | SF5 | |
| 14 | −39.29 | 16.62 | | |
| 15 | 7.95 | 2.7 | SSKN8 | |
| 16 | −7.25 | 0.6 | FD10 | |
| 17 | −277.86 | 4.49 | | |
| 18 Window (722) | Infinity | 1.0 | BK7 | |
| 19 | Infinity | 2.0 | | |
| 20 Window/ skin surface (724) | Infinity | 1.0 | BK7 | |
| 21 Image (725) | Infinity | 0.2 | | |

The first column lists the number of surfaces that interact with the light emanating from source 702. Columns 2–5 list the optical and physical characteristics of each element. In practice, the control of spacings and curvatures is important in achieving good performance. Tolerances on spacings can vary, but are preferably controlled to within 0.1 mm. The numerical apertures of the listed elements are also important. For example, the numerical aperture size of any given element controls how much light gets through the imaging system. This can be accounted for by the clear aperture (diameter of lenses which is used to transmit light) of the lens elements. Moreover, the focal length of each element is also important. The focal length of a given lens element is a function of the radius of curvature of each surface and the refractive index of the material used to make each element.

In this example, objective 717 comprises two achromatic doublet lenses, with each doublet lens having two lenses attached at a common surface. However, a single lens objective can also be utilized to achieve similar results as will be apparent to one of ordinary skill in the art given the present description. Objective 717 focuses the illumination beam onto window 724, just outside the field of view of image capturing means 760. The image beam propagates from a blood vessel (or capillary or tissue sample) 725, through objective 717, through beamsplitter 718, towards image capturing means 760, along an image path 707. Note that the illumination beam is incident upon skin surface outside the FOV of image capturing means 760.

The illumination intensity coupling efficiency of this example is about 98% on-axis and 95% off-axis. According to this embodiment of the present invention, this higher coupling efficiency allows for the utilization of a lower wattage bulb for light source 702. In addition, this embodiment of the present invention also has the advantages of reduced heat dissipation required and lower power consumption for light source 702. For example, using a 5 watt lamp as light source 702, device 700 generates a virtual source of illumination within the tissue region having an intensity of about 0.6 milliwatts (mW) (over the area of the illuminating ring) reaching the blood vessel or capillary being imaged onto image capturing means 760.

A further advantage of this embodiment is that the increased illumination can be used to achieve a higher signal to noise ratio for the image capturing means 760. This increased signal to noise ratio provides more accurate and stable analysis results. If a CCD camera is used as image capturing means 760, this increased signal to noise ratio allows the application of auto-shuttering for exposure control. Auto-shuttering requires the CCD camera to be receiving enough illumination to saturate the detector even for the darkest conditions of use. If the illumination level is high enough, the auto-shutter function can decrease the shutter exposure time to prevent saturation and achieve an optimal exposure level.

Overall, the axicon embodiment can provide more illumination at the object plane for a given light source radiant exitance while eliminating the angular orientation variations caused by tissue birefringence in background intensity and contrast. The axicon embodiment, as well as the obscuration embodiment, each reduce the effects of contrast reducing glare in the captured image. The axicon embodiment allows for reduced lamp power consumption, higher illumination levels at the camera sensor plane, reduced heat dissipation, and the potential use of smaller lamps. Having higher illumination levels at the detector plane provides for higher signal to noise ratios in a CCD camera or other detector, which allows for more accurate determination of measurable image characteristics such as image intensity distributions, and sub-surface feature profiles such as the width and density of blood veins and glands.

c. Third Embodiment

According to a third embodiment of the present invention, an imaging system comprises an improved folding mirror or beam splitter. Recall that in FIG. 2, a folding mirror or beam splitter 218 is used to redistribute light from the illumination system to the blood vessel, capillary, or tissue sample being imaged at the object plane. According to this embodiment, rather than using an obscuration or conical lens in combination with a standard 50% reflection 50% transmission beam splitter, an improved folding mirror can transform the illumination beam and project a high contrast illumination pattern onto the object plane. The improved folding mirror or beam splitter can be designed as a mirror that has a completely transmissive center (i.e., having 100% transmission at the wavelength of the illumination and/or image beam). With this approach, a high contrast illumination pattern is imaged onto the object plane and nearly 100% of the intensity of the image beam that reaches the folding mirror will be captured by the image capturing means.

The application of the improved folding mirror in this type of imaging system eliminates the need for a separate obscuration or other means of redistributing the light source. In addition, this type of configuration provides complete isolation between the light source and the image signal; as such, this embodiment has much improved signal to noise ratio. Moreover, in a preferred embodiment, the improved folding mirror can also be incorporated into the obscuration embodiment and/or the axicon embodiment devices discussed above. Thus, the intensity of the illumination beam incident upon the tissue region and the intensity of the image beam reaching the image capturing means can both be increased in a straightforward manner, thus increasing the overall efficiency of the in vivo imaging device.

FIG. 8A shows a block diagram layout of an in vivo imaging device 800. Device 800 utilizes an annular mirror as a folding mirror to provide a high contrast illumination pattern. Device 800 comprises an illumination system 803 and an image capturing means or detector 860 that share a common axis 807 through a single objective 817. An illumination axis 806 and image axis 807 are combined along axis 807 using a folding mirror 818, shown in FIG. 8B as a 100% reflecting mirror with an elliptical hole in its central region. Thus, a high contrast illumination pattern is reflected off folding mirror 818 and propagates along path 807, passing through objective 817 before reaching a tissue region 824.

Figure 8C:
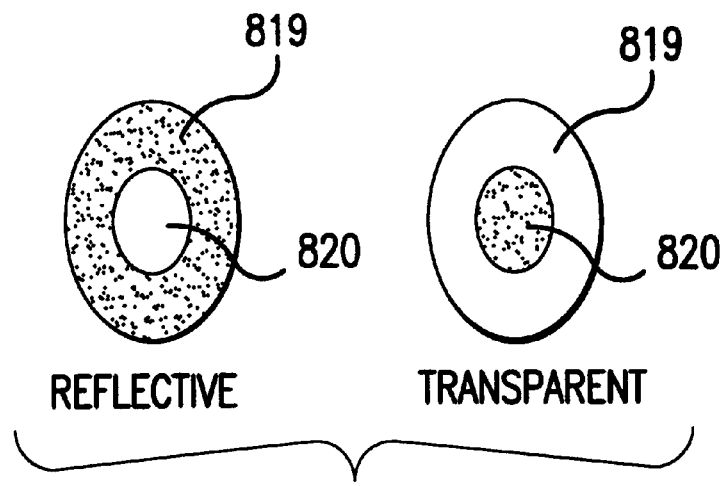
FIG. 8C shows exemplary dimensions for the folding mirror of the present invention.

In one preferred embodiment, in vivo imaging device 800 comprises an illumination system 803, an image forming objective 817 and a detector 860. Illumination system 803 comprises a light source 802 and a collimating lens 804, along with folding mirror 818, and objective 817. As shown in detail in FIG. 8B, folding mirror 818 is an annular mirror having a nearly 100% reflective surface (depending on the coating) around an elliptical annulus 819, and a clear aperture or center region 820 that is 100% transparent to the image beam and the illumination beam. The specific dimensions of the elliptical annulus and center regions will depend on the folding mirror's angle with respect to the image and illumination paths. In a preferred embodiment, the angle of folding mirror 818 with respect to illumination path 806 and image path 807 is about 45 degrees. For example, FIG. 8C shows exemplary dimensions for folding mirror 818 based on a 45 degree implementation. Other dimensions of the folding mirror and angles of incidence will be apparent to those of skill in the art given the present description.

Alternatively, folding mirror 818 can be a planer glass or plastic optical element having a first surface that is coated with a dichroic coating, having 100% transmission in the center region 820 and 100% reflection on annular outer portion 819. This implementation allows for nearly 100% reflection of the illuminating beam to the object plane while allowing for nearly 100% transmission of the image to the detector plane (excluding mirror and fresnel losses). Dichroic coatings are well known in the art and can be provided by many commercial coating vendors.

In yet another embodiment, folding mirror 818 can be a transparent glass plate having an etched, aluminized surface corresponding to annular outer portion 819. Further, a non-reflective second surface (not shown) of folding mirror 818 can be coated with an anti-reflection coating to minimize the loss of image signal reaching the detector. Another advantage of this folding mirror implementation is that folding mirror 818 does not have to be polarization sensitive. Thus, the imaging device utilizes all of the potential image beam. Other modifications to folding mirror 818 will be apparent to those of skill in the art given the present description. To further improve image quality, cross-polarizers can be utilized in device 800 in a similar manner as described above for the other embodiments of the present invention.

Figure 8D:
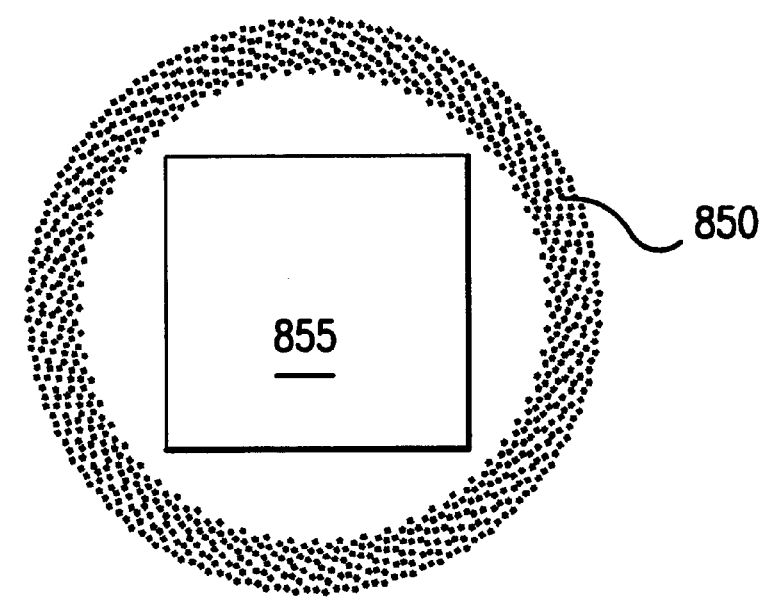
FIG. 8D shows an example illumination pattern incident on the object plane according to the present invention.

As mentioned above, in a preferred embodiment, the folding mirror or beam splitter can also be incorporated into the obscuration embodiment and the axicon embodiment devices discussed above. For example, folding mirror 818 can be substituted for beam splitter 218 (see FIG. 2), beam splitter 418 (see FIG. 4), or beam splitter 718 (see FIG. 7). For example, folding mirror 818 was substituted in a device similar to device 200. The predicted illumination pattern produced by this device is shown in FIG. 8D. The illumination incident on the object plane is similar to the illumination patterns described above, in that all the illumination is incident on the object plane outside the FOV of the image capturing means. In FIG. 8D, illumination pattern 850 is annular, where the inner diameter is about 1.5 mm. Thus, the entire illumination pattern incident upon the object plane lies outside the FOV of the image capturing means, illustrated by FOV 855.

Moreover, the use of folding mirror 818 in any of the above described embodiments can increase the overall imaging device efficiency. Assume that the standard beam splitter has a 50% transmission and a 50% reflection at the wavelength of interest. By replacing a standard beam splitter with folding mirror 818, the available illumination beam intensity at the tissue region increases by as much as a factor of two. Further, having 100% transmission of the image beam increases the intensity of the image signal reaching the image capturing means by a factor of two. Thus, the overall efficiency of the imaging system, in terms of image intensity per illumination intensity for the same light source, increases by about a factor of four.

Figure 9:
FIG. 9 shows an example image of a patient's vascular region taken by a device of the present invention.

As stated above, the illumination technique of the present invention greatly improves image quality by creating a virtual illumination source from within a living subject or patient. For example, FIG. 9 shows an example image obtained using a device based on the obscuration embodiment of the present invention. This image was obtained in the mucosal tissue under the tongue of a human test subject. Capillaries are visible as if illuminated in transmission. The globular structures visible are individual squamous cells.

d. Summary

An important feature of the present invention is the creation of a virtual source from within the tissue region being viewed by the image capturing means eliminates the need for fixing the imaging device in a particular position with respect to the tissue region being viewed. In other words, the device of the present invention is insensitive to angular rotations and other movements because scatter from near field birefringent tissue layers is substantially reduced. Moreover, the illumination techniques discussed herein allow for a flexible approach in instrument design. For example, the improved folding mirror discussed in the third embodiment can also be utilized in the obscuration embodiment or the axicon embodiment. Different light sources can be utilized depending on the types of measurements to be taken. Different optical elements can be utilized as the condensers, relay lenses, and objectives, as would be apparent to one of skill in the art given the present description.

7. Image Analysis

As mentioned above, image correcting and analyzing means are used to process the raw signal received by the image capturing means and generate an image, such as that shown in FIG. 9.

Several different types of image analysis techniques can be implemented according to the present invention. For example, a poly-chromatic correction can eliminate the effect of pigmentation of the tissue through which the light travels to illuminate the imaged portion of the vascular system. The tissue pigmentation will affect some wavelengths of light in the same manner, so that the tissue pigmentation effect is canceled out through use of a poly-chromatic correction. A velocity correction could be applied to extract moving cells from a stationary background. The velocity correction could be used alone, or in conjunction with a poly-chromatic correction.

There are only certain wavelengths which are absorbed equally by both arterial blood and by venous blood. A wavelength which is absorbed equally by both arterial and venous blood is called an isobestic point. One such isobestic point for hemoglobin is located at about 546 nm. In a preferred embodiment, $\lambda_1$ is selected so that it is located near the center of an absorption band for hemoglobin, and so that it is located near or at an isobestic point. A suitable $\lambda_1$ is 550 nm. In this manner, the hemoglobin concentration can be determined from reflected spectral imaging of a large vessel, irrespective of whether the large vessel is an artery carrying arterial blood or a vein carrying venous blood.

Figure 10:
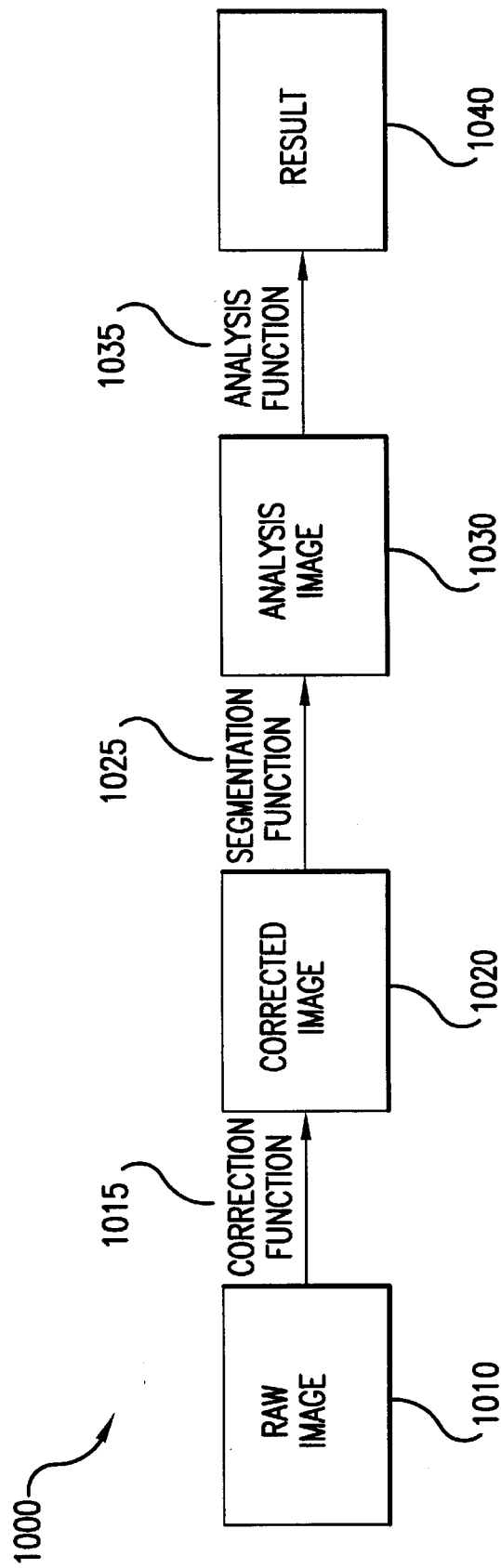
FIG. 10 shows an example image analysis method of the present invention.

For example, FIG. 10 illustrates an example process used to convert a raw image 1010 into a result 1040. By raw image is meant the image prior to application of a correction function 1015.

Correction function 1015 is applied to raw image 1010 to produce a corrected image 1020. Correction function 1015 normalizes raw image 1010 with respect to the image background. In one embodiment, correction function 1015 is implemented by way of a bi-chromatic correction. For a bi-chromatic correction, two wavelengths, $\lambda_1$ and $\lambda_2$, are selected. By subtracting the $\lambda_2$ image from the $\lambda_1$ image, all parameters that affect both $\lambda_1$ and $\lambda_2$ in the same manner cancel out, and are thus eliminated, in the resulting ($\lambda_1-\lambda_2$) image. The resulting ($\lambda_1-\lambda_2$) image incorporates the effect of only those parameters that affect $\lambda_1$ and $\lambda_2$ differently.

In another embodiment, correction function 1015 is implemented by way of a velocity or speed correction. For a velocity correction, corrected image 1020 is formed by taking the difference between raw image 1010 at a time $t_0$ and at a time $t_1$. For this purpose, means can be provided to pulse the light, and/or shutter an image capturing means such as a camera, so that two different images in time are obtained. A velocity correction allows a moving portion of raw image 1010 to be extracted from a stationary portion of raw image 1010. In this manner, corrected image 1020 is formed to contain either the moving portion or the stationary portion of raw image 1010.

A segmentation function 1025 is applied to corrected image 1020 to form an analysis image 1030. Segmentation function 1025 segments or separates a scene of interest from corrected image 1020 to form analysis image 1030. An analysis function 1035 is applied to analysis image 1030 to produce result 140. The scene of interest segmented by segmentation function 1025 can depend upon the type of analysis performed by analysis function 1035. In this manner, corrected image 1020 may contain many scenes of interests that are segmented differently by various segmentation functions. Further detailed description of several specific methods of performing image analysis is provided in the above-referenced '363 application.

Figure 11:
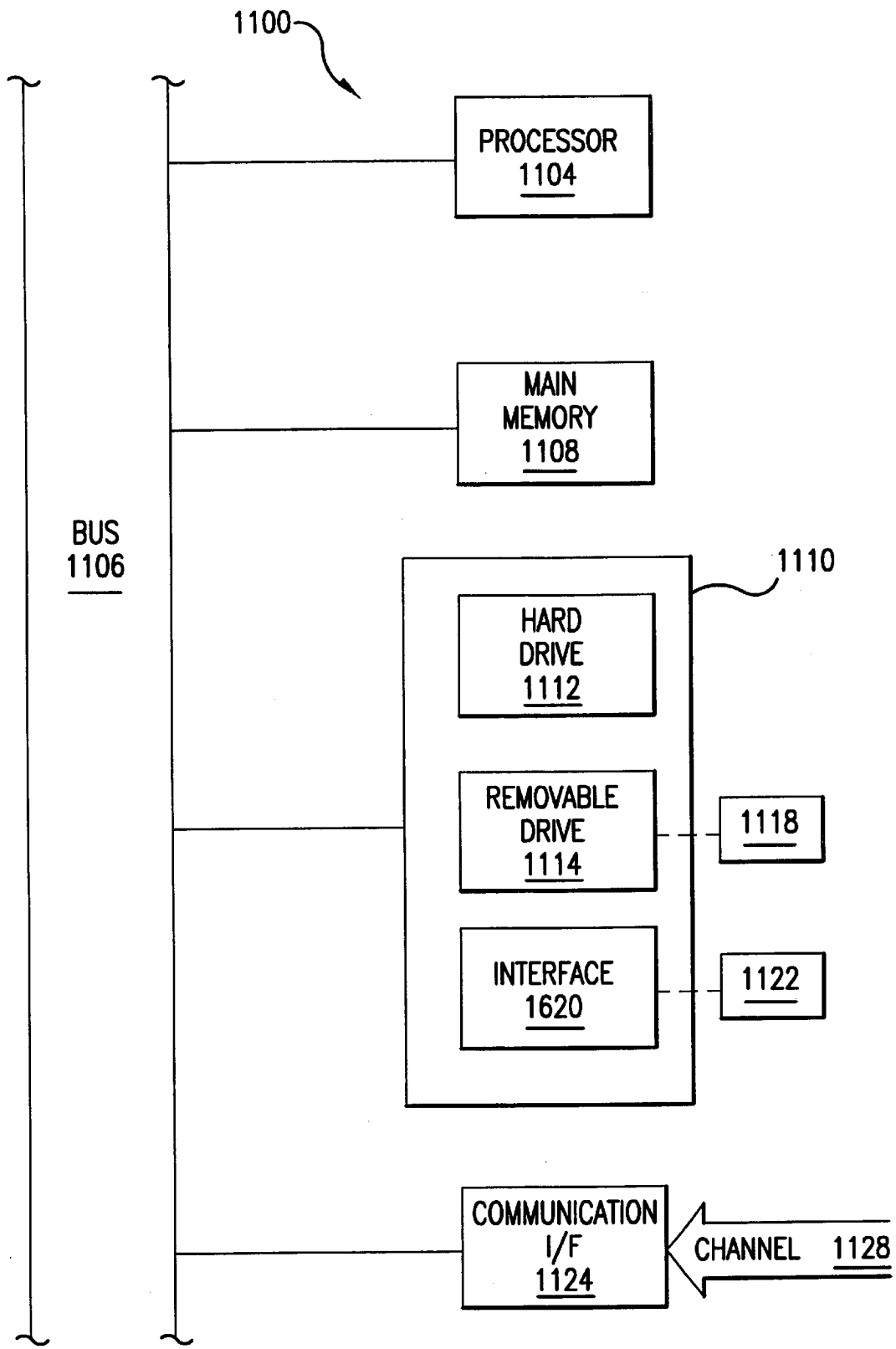
FIG. 11 shows a block diagram of a computer system suitable for use in the present invention.

The method illustrated in FIG. 10 can be used to carry out non-invasive in vivo analysis of blood parameters for the purpose of diagnosis or monitoring. An exemplary image correcting and analyzing means for use in the present invention, such as image correcting and analyzing means 280 described above in FIG. 2, is shown as a computer system 1100 in FIG. 11. Computer system 1100 includes one or more processors, such as processor 1104. Processor 1104 is connected to a communication bus 1106. Various software embodiments are described in terms of this exemplary computer system. After reading this description, it will become apparent to a person skilled in the relevant art how to implement the invention using other computer systems and/or computer architectures.

Computer system 1100 also includes a main memory 1108, preferably random access memory (RAM), and can also include a secondary memory 1110. Secondary memory 1110 can include, for example, a hard disk drive 1112 and/or a removable storage drive 1114, representing a floppy disk drive, a magnetic tape drive, an optical disk drive, etc. Removable storage drive 1114 reads from and/or writes to a removable storage unit 1118 in a well known manner. Removable storage unit 1118 represents a floppy disk, magnetic tape, optical disk, etc. which is read by and written to by removable storage drive 1114. As will be appreciated, removable storage unit 1118 includes a computer usable storage medium having stored therein computer software and/or data.

In alternative embodiments, secondary memory 1110 may include other similar means for allowing computer programs or other instructions to be loaded into computer system 1100. Such means can include, for example, a removable storage unit 1122 and an interface 1120. Examples of such can include a program cartridge and cartridge interface (such as that found in video game devices), a removable memory chip (such as an EPROM, or PROM) and associated socket, and other removable storage units 1122 and interfaces 1120 which allow software and data to be transferred from removable storage unit 1122 to computer system 1100.

Computer system 1100 can also include a communications interface 1124. Communications interface 1124 allows software and data to be transferred between computer system 1100 and external devices, such as image capturing means 260. Examples of communications interface 1124 can include a modem, a network interface (such as an Ethernet card), a communications port, a PCMCIA slot and card, etc. Software and data transferred via communications interface 1124 are in the form of signals which can be electronic, electromagnetic, optical or other signals capable of being received by communications interface 1124. For example, an image signal is provided to communications interface via a channel 1128. Channel 1128 carries the signal and can be implemented using wire or cable, fiber optics, a phone line, a cellular phone link, an RF link and other communications channels.

In this description, the terms "computer program medium" and "computer usable medium" are used to generally refer to media such as removable storage device 1118, a hard disk installed in hard disk drive 1112, and signals provided via channel 1128. These computer program products are means for providing software to computer system 1100.

Computer programs (also called computer control logic) are stored in main memory 1108 and/or secondary memory 1110. Computer programs can also be received via communications interface 1124. Such computer programs, when executed, enable computer system 1100 to perform the features of the present invention as discussed herein. In particular, the computer programs, when executed, enable processor 1104 to perform the image analysis features of the present invention. Accordingly, such computer programs represent controllers of computer system 1100.

In an embodiment where the invention is implemented using software, the software may be stored in a computer program product and loaded into computer system 1100 using removable storage drive 1114, hard drive 1112 or communications interface 1124. The control logic (software), when executed by the processor 1104, causes processor 1104 to perform the image analysis functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

8. Applications

In summary, the device and method of the present invention can be used to determine various characteristics of a vascular system in a non invasive manner. In a practical application of the present invention, the embodiments described in detail above can be implemented in a compact device or probe. The following description is not meant to limit the applications of the present invention. It is provided as an exemplary utilization of the present invention. Other alterations or modification will be apparent to those of skill in the art based on the present invention.

Figure 12A:
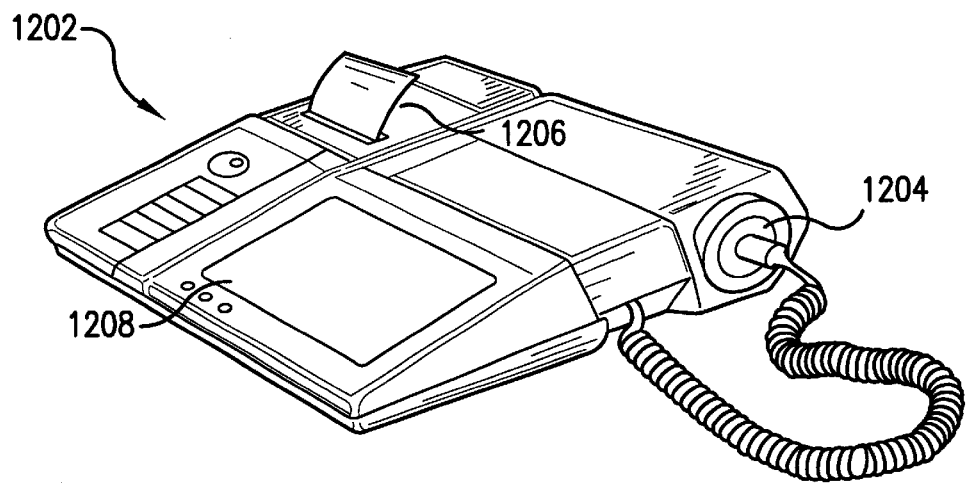
FIGS. 12A and 12B show embodiments of the present invention suitable for use with a subject.
Figure 12B:
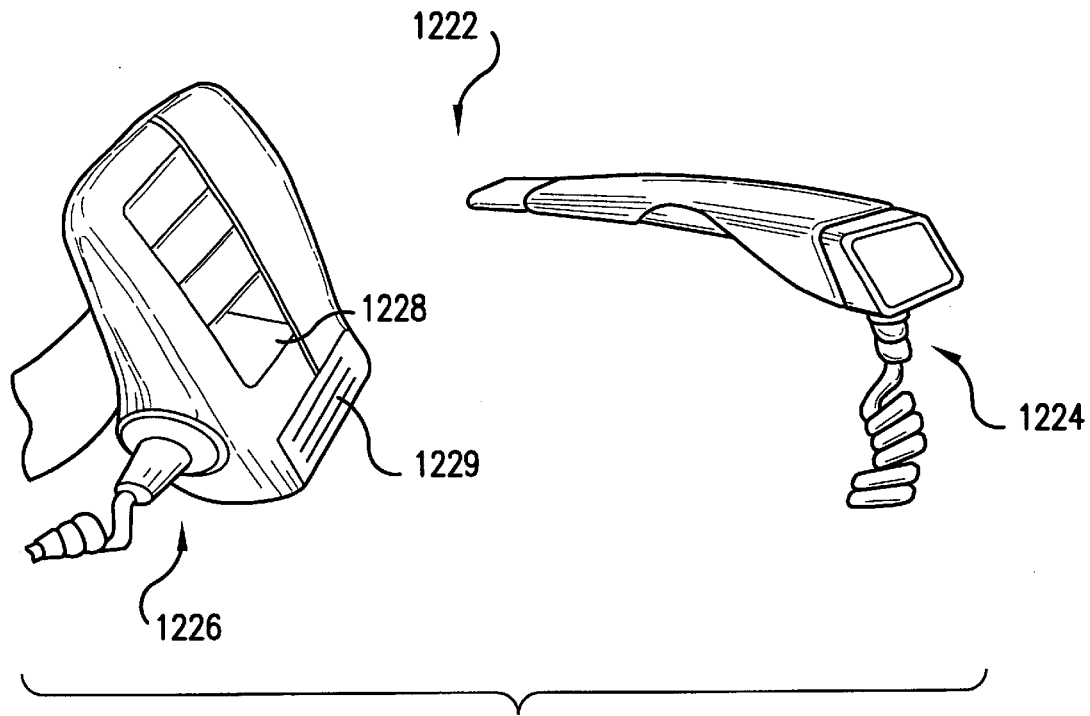

FIGS. 12A and 12B show embodiments of the present invention suitable for use with a subject for performing non-invasive in vivo analysis. FIG. 12A shows a console unit 1202 that contains a probe 1204, a printer 1206, and a processing and storage unit 1208. Probe 1204 is used to image the portion of the subject's vascular system, such as the inside of the lower lip. An index matching medium, such as ethyl cellulose or a sugar syrup, is preferably applied to probe 1204 to provide a good optical contact or optical seal between probe 1204 and the inside of the lower lip.

Probe 1204 is preferably equipped with the elements shown in FIGS. 2, 4, 7, and/or 8A (or in any combination thereof). For example, with respect to FIG. 2, probe 1204 is equipped with a light source 202 through one or more image capturing means. To ensure optimal performance of the apparatus of the present invention, there should not be anything in the light path between polarizer 210 and polarizer 220 that de-polarizes the light. For example, the presence of dust in the light path between polarizer 1510 and polarizer 1520 will degrade the performance of the apparatus. Further, the components of probe 1204 are preferably made of non-depolarizing material so that the materials will not de-polarize the light. A particularly preferred material for the components of probe 1204 in the light path is a non-depolarizing, non-birefringent plastic material available from Kodak with the trade name KODACEL. Other suitable materials for components in the light path are glass or quartz. In addition, the interior of probe 1204 can be coated with an anti-scatter coating such as Martin Black or Orlando Black, which are available from commercial coating vendors. These anti-scatter coatings can be utilized to further reduce the internal scatter of probe 1204. A preferred material for the imaging end of probe 1204 is glass. The image signal is transmitted from probe 1204 to processing and storage unit 1208 for processing and storage.

FIG. 12B shows a mobile unit 1222. Mobile unit 1222 includes a probe 1224 and a belt unit 1226. Probe 1224 can be configured in a similar manner to probe 1204 shown in FIG. 12A. Belt unit 1226 includes a data storage and transmission unit 1228. Data storage and transmission unit 1228 receives signals from probe 1224. These signals can be stored by data storage and transmission unit 1228 for processing at a later time. Alternatively, these signals can be transmitted by data storage and transmission unit 1228 to a central processing station (not shown) for processing and storage. The central processing station can be configured to provide permanent storage for the processed data, as well as to print and display the results in a well known manner. Belt unit 1226 also includes a location 1229 for batteries or other suitable power supply.

The in vivo apparatus of the present invention can be used to carry out the methods of the present invention discussed above. Particularly, the in vivo apparatus can be used to determine hemoglobin and bilirubin concentrations per unit volume of blood. The in vivo apparatus can also be used to determine the hematocrit and the mean cell volume. The in vivo apparatus can also be used to determine the number of white blood cells and the number of platelets per unit volume of blood. For determining the number of cells, such as white blood cells or platelets, the light source is configured as a pulsed light source or flash to "stop action" in the analysis image so the count can be made. The stop action achieved with the pulsed light source avoids the blurring associated with movement in the analysis image. The pulsed light source is preferably synchronized with the frame rate of the image capturing means. Stop action can also be achieved by controlling shuttering on the image capturing means. A stop action image is preferred any time a count of cells is to be made in the analysis image. A stop action image can also be used to determine other non-cell-count parameters, such as Hb or Hct. However, such other parameters such as Hb and Hct can be determined with a non-stop action image as well. Other types of image analysis consistent with the examples discussed above will be apparent to those of skill in the art based on the present description.

By using the device and method of the present invention to provide a spectral image of large vessels, the hemoglobin (Hb), hematocrit (Hct), and white blood cell count (WBC) parameters can be directly determined. By using the device and method of the present invention to provide a spectral image of small vessels, mean cell volume (MCV), mean cell hemoglobin concentration (MCHC), and platelet count (Plt) can be directly determined.

9. Conclusion

While various embodiments of the present invention have been described above, it should be understood that they have been presented by way of example only, and not limitation. The illumination techniques of the present invention can be used in any analytical, in vivo, or in vitro application that requires optically measuring or visually observing characteristics of an object. Thus, the breadth and scope of the present invention should not be limited by any of the above-described exemplary embodiments, but should be defined only in accordance with the following claims and their equivalents.

What is claimed is:

1. An apparatus for detecting optical characteristics of a sub-surface object located in the region of an object plane, comprising:

a light source for providing an illumination beam;

an illumination system that transforms said illumination beam into an illumination pattern having a high intensity portion and a low intensity portion and projects said high intensity portion onto the sub-surface object substantially outside a desired portion of the sub-surface object to be imaged; and an image capturing device for detecting an image of the desired portion of the sub-surface object, said image being formed by scattered illumination from said illumination pattern that is transmitted through the sub-surface object to said image capturing device, wherein said illumination system projects said high intensity region outside a field of view of said image capturing device at the object plane and projects said low intensity region within the field of view of said image capturing device.

2. The apparatus of claim 1, further comprising a condenser disposed between said light source and said object plane to collimate said illumination beam.

3. The apparatus of claim 1, said illumination system comprising a folding mirror disposed between said light source and the object plane, said folding mirror including a surface having a substantially reflective outer portion and a substantially transmissive inner portion.

4. The apparatus of claim 1, further comprising an objectived disposed between the object plane and said image capturing device along said image path for magnifying said image onto said image capturing device.

5. The apparatus of claim 4, wherein said illumination system comprises:

an illumination pattern generator disposed between said light source and the object plane to transform said illumination beam into a dual intensity pattern having said high intensity portion and said low intensity portion;

a projection lens disposed between said illumination pattern generator and the object plane that projects said high intensity pattern onto the object plane; and a folding mirror, disposed between said light source and the object plane and disposed between the object plane and the image capturing device, to direct said projected high intensity illumination portion along said image path onto the object plane.

6. The apparatus of claim 4, wherein said illumination pattern generator comprises an obscuration disposed between said light source and said optical element, said obscuration substantially blocking a first portion of said illumination beam to form said low intensity portion, and permitting substantially unobstructed passage of a second portion of said illumination beam to form said high intensity portion.

7. The apparatus of claim 6, wherein said obscuration is disposed along said illumination path substantially in the plane of a first aperture, wherein an outer diameter of said obscuration corresponds to said field of view of said image capturing device, and wherein said projection lens and said objective images said obscuration onto the object plane.

8. The apparatus claim 5, wherein said illumination pattern generator comprises:

a conical lens disposed between said light source and said projection lens, said conical lens redistributing said illumination beam into an annular pattern projected onto the object plane by said projection lens, wherein said annular pattern has a low intensity central portion and a high intensity outer portion.

9. The apparatus of claim 8, wherein said conical lens is an axicon.

10. The apparatus of claim 5, wherein said illumination pattern generator comprises a conical grating disposed between said light source and said projection lens, said conical grating redistributing said illumination beam into an annular pattern projected onto the object plane by said projection lens, wherein said annular pattern has a low intensity central portion and a high intensity outer portion.

11. The apparatus of claim 5, wherein said illumination pattern generator comprises an optical element disposed between said light source and said projection lens, said optical element having a hologram coated onto a surface of said optical element for redistributing said illumination beam into an annular pattern projected onto the object plane by said projection lens, wherein said annular pattern has a low intensity central portion and a high intensity outer portion.

12. The apparatus of claim 5, further comprising:
a first polarizer disposed between said light source and said folding mirror for polarizing said illumination beam from said light source; and
a second polarizer having a plane of polarization substantially orthogonal to a plane of polarization of said first polarizer and disposed along said image path between the folding mirror and said image capturing device,.

13. A spectral imaging apparatus for non-invasive, in vivo imaging of a subject's tissue and blood, comprising:
a light source for illuminating a region of interest;
means for transforming light emanating from said light source into an illumination pattern having a low intensity portion and a high intensity portion;
projection means for projecting said low intensity portion of said illumination pattern onto an object substantially within the region of interest and beneath a surface of the region of interest and for projecting said high intensity portion of said illumination pattern onto the object substantially outside the region of interest; and
an image capturing device for capturing an image of the region of interest formed by scattered illumination from said high intensity illumination portion that is transmitted through the object and the region of interest to said image capturing device.

14. The apparatus of claim 13, wherein said projection means directs said high intensity portion of said illumination pattern to a portion of said region of interest outside a field of view of said image capturing means.

15. The apparatus of claim 14, wherein light from said high intensity portion of said illumination pattern interacts with matter within said region of interest and is scattered by one or more scattering events, thereby forming a sub-surface illumination source to illuminate said object.

16. The apparatus of claim 15, wherein said image is formed by a substantial portion of said sub-surface illumination source being transmitted through said object along said image path.

17. A method for creating a source of illumination in a sub-surface region of an object that contains an area of interest, wherein the area of interest is illuminated from all directions about an object plane wherein the object is located, wherein an image of the area of interest is detected by an image capturing device, comprising the steps of:
(a) transforming light from a light source into an illumination pattern having a high intensity portion and a low intensity portion;
(b) directing said illumination pattern onto a surface of the object such that said high intensity portion of said illumination pattern is incident upon the object plane substantially outside a field of view of the image capturing device and said low intensity portion is incident upon the object plane substantially within the field of view of the image capturing device; and
(d) detecting scattered light that interacts with the area of interest with the image capturing device, wherein said high intensity portion of said illumination pattern undergoes one or more scattering events in the sub-surface region.

18. The method of claim 17, further comprising the step of:
(e) performing a transmission measurement of said sub-surface region.

19. The method of claim 18, wherein step (b) further comprises:
providing a folding mirror having a first surface that includes a substantially reflective outer portion and a substantially transmissive inner portion, wherein light reflected off said substantially reflective outer portion forms said high intensity portion of said illumination pattern.

20. The method of claim 17, wherein step (b) further comprises:
blocking a portion of said light from said source to form said low intensity portion of said illumination pattern.

21. The method of claim 15, wherein step (b) further comprises:
providing an optical element to redistribute said light into an annular pattern which corresponds to said illumination pattern.

22. A spectral imaging apparatus for non-invasive, in vivo imaging of mammalian tissue and blood in a living body, comprising:
a light source for providing an illumination beam;
an illumination system that transforms said illumination beam into an illumination pattern having a high intensity portion and a low intensity portion and projects said illumination pattern below the surface of the tissue; and
an image capturing device for detecting an image of the desired portion of the sub-surface region, said image being formed by scattered illumination from said illumination pattern that is transmitted through the sub-surface region to said image capturing device,
wherein said illumination system projects said high intensity portion substantially outside a field of view of said image capturing device at the surface of the tissue and projects said low intensity portion substantially within the field of view of said image capturing device.

23. The apparatus of claim 22, wherein said illumination system comprises:
an illumination pattern generator disposed between said light source and the surface of the tissue to transform said illumination beam into a dual intensity pattern having said high intensity portion and said low intensity portion;
a projection lens disposed between said illumination pattern generator and the surface of the tissue that projects said high intensity portion toward the surface of the tissue; and a folding mirror, disposed between said light source and the surface of the tissue and disposed between the surface of the tissue and the image capturing device, to direct said projected high intensity illumination portion onto the surface of the tissue and to direct scattered light from the subsurface region of the tissue to said image capturing device.

24. The apparatus of claim 23, wherein said illumination pattern generator comprises an obscuration disposed between said light source and said optical element, said obscuration substantially blocking a first portion of said illumination beam to form said low intensity portion, and permitting substantially unobstructed passage of a second portion of said illumination beam to form said high intensity portion.

25. The apparatus of claim 24, wherein said obscuration is disposed along said illumination path substantially in the plane of a first aperture, wherein an outer diameter of said obscuration corresponds to said field of view of said image capturing device, and wherein said projection lens and said objective images said obscuration onto the object plane.

26. The apparatus of claim 23, wherein said illumination pattern generator comprises:
a conical lens disposed between said light source and said projection lens, said conical lens redistributing said illumination beam into an annular pattern projected onto the object plane by said projection lens, wherein said annular pattern has a low intensity central portion and a high intensity outer portion.

27. The apparatus of claim 16, wherein said conical lens is an axicon.

28. The apparatus of claim 23, wherein said illumination pattern generator comprises a conical grating disposed between said light source and said projection lens, said conical grating redistributing said illumination beam into an annular pattern projected onto the object plane by said projection lens, wherein said annular pattern has a low intensity central portion and a high intensity outer portion.

29. The apparatus of claim 23, wherein said illumination pattern generator comprises an optical element disposed between said light source and said projection lens, said optical element having a hologram coated onto a surface of said optical element for redistributing said illumination beam into an annular pattern projected onto the object plane by said projection lens, wherein said annular pattern has a low intensity central portion and a high intensity outer portion.

30. The apparatus of claim 23, further comprising:
a first polarizer disposed between said light source and said folding mirror for polarizing said illumination beam from said light source; and
a second polarizer having a plane of polarization substantially orthogonal to a plane of polarization of said first polarizer and disposed along said image path between the folding mirror and said image capturing device.

* * * * *